(12) United States Patent
Patel et al.

(10) Patent No.: US 12,310,978 B2
(45) Date of Patent: May 27, 2025

(54) COMPOSITION AND METHOD FOR ORAL DELIVERY OF ANDROGEN PRODRUGS

(71) Applicant: Lipocine Inc., Salt Lake City, UT (US)

(72) Inventors: Mahesh V. Patel, Salt Lake City, UT (US); Nachiappan Chidambaram, Sandy, UT (US); Satish K. Nachaegari, Holladay, UT (US)

( * ) Notice: Subject to any disclaimer, the term of this patent is extended or adjusted under 35 U.S.C. 154(b) by 981 days.

(21) Appl. No.: 16/726,572

(22) Filed: Dec. 24, 2019

(65) Prior Publication Data
US 2020/0222425 A1    Jul. 16, 2020

Related U.S. Application Data

(63) Continuation of application No. 15/861,492, filed on Jan. 3, 2018, now abandoned, which is a continuation of application No. 15/183,691, filed on Jun. 15, 2016, now abandoned.

(60) Provisional application No. 62/175,931, filed on Jun. 15, 2015, provisional application No. 62/253,292, filed on Nov. 10, 2015.

(51) Int. Cl.
| | | |
|---|---|---|
| *A61K 31/568* | (2006.01) | |
| *A61J 1/03* | (2023.01) | |
| *A61J 1/06* | (2006.01) | |
| *A61J 1/10* | (2006.01) | |
| *A61J 7/00* | (2006.01) | |
| *A61K 9/00* | (2006.01) | |
| *A61K 9/48* | (2006.01) | |

(52) U.S. Cl.
CPC ............. *A61K 31/568* (2013.01); *A61J 1/035* (2013.01); *A61J 1/06* (2013.01); *A61J 1/10* (2013.01); *A61J 7/0076* (2013.01); *A61K 9/0053* (2013.01); *A61K 9/4858* (2013.01); *A61K 9/4866* (2013.01)

(58) Field of Classification Search
CPC .. A61K 31/568; A61K 9/0053; A61K 9/4858; A61K 9/4866; A61J 1/035; A61J 1/06; A61J 1/10; A61J 7/0076
See application file for complete search history.

(56) References Cited

U.S. PATENT DOCUMENTS

| | | |
|---|---|---|
| 2,680,749 A | 6/1954 | Cawley et al. |
| 2,742,487 A | 4/1956 | Robledano |
| 3,097,139 A | 7/1963 | Thorp |
| 3,097,144 A | 7/1963 | Banker |
| 3,164,520 A | 1/1965 | Huber |
| 3,266,991 A | 8/1966 | Wettstein et al. |
| 3,510,561 A | 5/1970 | Koh |
| 4,098,802 A | 7/1978 | Van der Vies |
| 4,147,783 A | 4/1979 | Van der Vies |
| 4,156,719 A | 5/1979 | Sezaki et al. |
| 4,177,188 A | 12/1979 | Hansen et al. |
| 4,196,188 A | 4/1980 | Besins |
| 4,220,599 A | 9/1980 | Van der Vies |
| 4,239,754 A | 12/1980 | Sache et al. |
| 4,388,307 A | 6/1983 | Cavanak |
| 4,439,432 A | 3/1984 | Peat |
| 4,572,915 A | 2/1986 | Crooks |
| 4,579,730 A | 4/1986 | Kidron et al. |
| 4,628,052 A | 12/1986 | Peat |
| 4,628,098 A | 12/1986 | Nohara et al. |
| 4,654,327 A | 3/1987 | Teng |
| 4,656,161 A | 4/1987 | Herr |
| 4,689,333 A | 8/1987 | Nohara et al. |
| 4,695,450 A | 9/1987 | Bauer |
| 4,703,042 A | 10/1987 | Bodor |
| 4,713,246 A | 12/1987 | Begum et al. |
| 4,717,569 A | 1/1988 | Harrison et al. |
| 4,717,596 A | 1/1988 | Barbee et al. |
| 4,719,239 A | 1/1988 | Muller et al. |
| 4,727,109 A | 2/1988 | Schmidt et al. |
| 4,731,384 A | 3/1988 | Dell |
| 4,795,327 A | 1/1989 | Gaylord et al. |
| 4,832,952 A | 5/1989 | Hersh et al. |
| 4,834,965 A | 5/1989 | Martani et al. |
| 4,849,227 A | 7/1989 | Cho |
| 4,867,984 A | 9/1989 | Patel |
| 4,874,795 A | 10/1989 | Yesair |
| 4,880,634 A | 11/1989 | Speiser |
| 4,895,726 A | 1/1990 | Curtet et al. |
| 4,897,269 A | 1/1990 | Mezei |
| 4,900,734 A | 2/1990 | Maxson et al. |
| 4,925,672 A | 5/1990 | Gremm |
| 4,944,949 A | 7/1990 | Story |
| 4,961,890 A | 10/1990 | Bover |
| 4,963,540 A | 10/1990 | Maxson et al. |
| 4,994,439 A | 2/1991 | Longenecker et al. |
| 5,023,108 A | 6/1991 | Bageria et al. |
| 5,026,560 A | 6/1991 | Makino et al. |
| 5,035,891 A | 7/1991 | Runkel et al. |
| 5,045,321 A | 9/1991 | Makino et al. |
| 5,057,319 A | 10/1991 | Gottwald |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |

(Continued)

FOREIGN PATENT DOCUMENTS

| | | |
|---|---|---|
| CA | 2295028 A1 | 1/1999 |
| CA | 2302735 A1 | 1/2000 |

(Continued)

OTHER PUBLICATIONS

Yin (Year: 2012).*

(Continued)

*Primary Examiner* — Jeffrey S Lundgren
*Assistant Examiner* — Ibrahim D Bori
(74) *Attorney, Agent, or Firm* — Michael R. Schramm

(57) ABSTRACT

Provided oral testosterone undecanoate compositions can be administered to hypogonadal males with a meal without the fat content of the meal substantially effecting bioavailability.

20 Claims, No Drawings

(56) References Cited

U.S. PATENT DOCUMENTS

| | | |
|---|---|---|
| 5,104,656 A | 4/1992 | Seth et al. |
| 5,120,710 A | 6/1992 | Liedtke |
| 5,140,021 A | 8/1992 | Maxon et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Geyer et al. |
| 5,384,133 A | 1/1995 | Boyes et al. |
| 5,389,382 A | 2/1995 | List et al. |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | DeBoeck et al. |
| 5,560,931 A | 10/1996 | Eickhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wright |
| 5,633,015 A | 5/1997 | Gillis et al. |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savatano et al. |
| 5,686,105 A | 11/1997 | Kelm et al. |
| 5,688,761 A | 11/1997 | Owen et al. |
| 5,698,155 A | 12/1997 | Grosswald et al. |
| 5,707,648 A | 1/1998 | Yiv |
| 5,714,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,776,495 A | 7/1998 | Duclos et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,916,589 A | 6/1999 | Hauer et al. |
| 5,922,355 A | 7/1999 | Parikh et al. |
| 5,948,773 A | 9/1999 | Akiyama et al. |
| 5,948,825 A | 9/1999 | Takahashi et al. |
| 5,962,014 A | 10/1999 | Hauer et al. |
| 5,962,017 A | 10/1999 | Hauer et al. |
| 5,965,161 A | 10/1999 | Osblack |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kerc et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamm et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |
| 6,228,400 B1 | 5/2001 | Lee |
| 6,248,363 B1 | 6/2001 | Patel et al. |
| 6,255,100 B1 | 7/2001 | Ko |
| 6,267,985 B1 | 7/2001 | Chen et al. |
| 6,287,594 B1 | 9/2001 | Wilson |
| 6,294,192 B1 | 9/2001 | Patel et al. |
| 6,296,876 B1 | 10/2001 | Odidi et al. |
| 6,299,904 B1 | 10/2001 | Shimizu et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder et al. |
| 6,328,994 B1 | 12/2001 | Shimizu et al. |
| 6,340,471 B1 | 1/2002 | Kershman et al. |
| 6,342,246 B2 | 1/2002 | Johnson et al. |
| 6,361,796 B1 | 3/2002 | Rudnic et al. |
| 6,368,634 B1 | 4/2002 | Remon |
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambuhl et al. |
| 6,444,225 B1 | 9/2002 | Sherman |
| 6,447,806 B1 | 9/2002 | Gassmann et al. |
| 6,451,339 B2 | 9/2002 | Patel et al. |
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |
| 6,468,559 B1 | 10/2002 | Chen et al. |
| 6,475,519 B1 | 11/2002 | Minzer et al. |
| 6,503,894 B1 | 1/2003 | Dudley et al. |

(56) References Cited

U.S. PATENT DOCUMENTS

| | | |
|---|---|---|
| 6,531,139 B1 | 3/2003 | Gao et al. |
| 6,569,463 B2 | 5/2003 | Patel et al. |
| 6,589,552 B2 | 7/2003 | Stamm et al. |
| 6,589,562 B1 | 7/2003 | Shefer et al. |
| 6,623,755 B2 | 9/2003 | Chen et al. |
| 6,630,134 B1 | 10/2003 | Klein |
| 6,652,880 B1 | 11/2003 | Aylwin et al. |
| 6,660,286 B1 | 12/2003 | Lambert et al. |
| 6,665,880 B2 | 12/2003 | Pope |
| 6,667,048 B1 | 12/2003 | Lambert et al. |
| 6,692,766 B1 | 2/2004 | Rubinstein et al. |
| 6,696,482 B2 | 2/2004 | Schenoy et al. |
| 6,720,001 B2 | 4/2004 | Chen et al. |
| 6,737,082 B1 | 5/2004 | Picornell Darder |
| 6,761,903 B2 | 7/2004 | Chen et al. |
| 6,881,745 B2 | 4/2005 | Hayes et al. |
| 6,887,493 B2 | 5/2005 | Shefer et al. |
| 6,913,244 B1 | 7/2005 | Atkinson et al. |
| 6,923,988 B2 | 8/2005 | Patel et al. |
| 6,977,083 B1 | 12/2005 | Huebler et al. |
| 6,982,281 B1 | 1/2006 | Chen et al. |
| 7,025,979 B2 | 4/2006 | Neischlag et al. |
| 7,138,389 B2 | 11/2006 | Amory et al. |
| 7,374,779 B2 | 5/2008 | Chen et al. |
| 7,658,944 B2 | 2/2010 | Holm et al. |
| 7,718,640 B2 | 5/2010 | Hubler et al. |
| 8,241,664 B2 | 8/2012 | Dudley et al. |
| 8,338,395 B2 | 12/2012 | Hubler et al. |
| 8,778,922 B2 | 7/2014 | Giliyar et al. |
| 8,865,695 B2 | 10/2014 | Giliyar et al. |
| 9,034,858 B2 | 5/2015 | Giliyar et al. |
| 9,205,057 B2 | 12/2015 | Giliyar et al. |
| 9,358,241 B2 | 6/2016 | Giliyar et al. |
| 9,498,485 B2 | 6/2016 | Patel et al. |
| 9,480,690 B2 | 11/2016 | Giliyar et al. |
| 9,757,390 B2 | 9/2017 | Giliyar et al. |
| 9,943,527 B2 | 4/2018 | Giliyar et al. |
| 9,949,985 B2 | 4/2018 | Giliyar et al. |
| 10,226,473 B2 | 3/2019 | Giliyar et al. |
| 10,561,615 B2 | 2/2020 | Chickmath et al. |
| 10,716,794 B2 | 7/2020 | Giliyar et al. |
| 10,799,513 B2 | 10/2020 | Giliyar et al. |
| 10,881,671 B2 | 1/2021 | Giliyar et al. |
| 10,973,833 B2 | 4/2021 | Giliyar et al. |
| 11,052,096 B2 | 7/2021 | Giliyar et al. |
| 11,311,555 B2 | 4/2022 | Giliyar et al. |
| 11,364,249 B2 | 6/2022 | Giliyar et al. |
| 11,364,250 B2 | 6/2022 | Giliyar et al. |
| 11,433,083 B2 | 9/2022 | Giliyar et al. |
| 2001/0018069 A1 | 8/2001 | Johnson et al. |
| 2002/0006443 A1 | 1/2002 | Curatolo et al. |
| 2002/0013304 A1 | 1/2002 | Wilson et al. |
| 2002/0058066 A1 | 5/2002 | Tomohira et al. |
| 2002/0068693 A1 | 6/2002 | Jeng et al. |
| 2002/0085978 A1 | 7/2002 | Buenafe et al. |
| 2002/0102301 A1 | 8/2002 | Schwarz |
| 2002/0103139 A1 | 8/2002 | Weisspapir et al. |
| 2002/0183296 A1 | 12/2002 | Dudley et al. |
| 2003/0022875 A1 | 1/2003 | Wilson et al. |
| 2003/0072798 A1 | 4/2003 | Schwarz et al. |
| 2003/0077297 A1 | 4/2003 | Chen et al. |
| 2003/0082215 A1 | 5/2003 | Lemut et al. |
| 2003/0104048 A1 | 6/2003 | Patel et al. |
| 2003/0109508 A1 | 6/2003 | Yanni et al. |
| 2003/0209508 A1 | 6/2003 | Yanni et al. |
| 2003/0175326 A1 | 9/2003 | Thombre |
| 2003/0180352 A1 | 9/2003 | Patel et al. |
| 2003/0181431 A1 | 9/2003 | Hodgen |
| 2003/0186892 A1 | 10/2003 | Taneja |
| 2003/0216260 A1 | 11/2003 | Ruther |
| 2003/0216360 A1 | 11/2003 | Grawe et al. |
| 2003/0228358 A1 | 12/2003 | Perlman et al. |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0002482 A1 | 1/2004 | Dudley et al. |
| 2004/0048896 A1 | 3/2004 | Phillips |
| 2004/0127476 A1 | 7/2004 | Kershaman et al. |
| 2005/0031693 A1 | 2/2005 | Babcock et al. |
| 2005/0032762 A1 | 2/2005 | Hubler et al. |
| 2005/0070516 A1 | 3/2005 | Wilson |
| 2005/0080075 A1 | 4/2005 | Nichols et al. |
| 2005/0096296 A1 | 5/2005 | Fikstad et al. |
| 2005/0096365 A1 | 5/2005 | Fikstad et al. |
| 2005/0100608 A1 | 5/2005 | Ebert |
| 2005/0101517 A1 | 5/2005 | De Nijs et al. |
| 2005/0171193 A1 | 8/2005 | Chen et al. |
| 2005/0176692 A1 | 8/2005 | Amory et al. |
| 2005/0209345 A1 | 9/2005 | Charman |
| 2005/0220825 A1 | 10/2005 | Funke et al. |
| 2005/0269251 A1 | 12/2005 | Cork |
| 2005/0287203 A1 | 12/2005 | De Nijs et al. |
| 2005/0287212 A1 | 12/2005 | Dong et al. |
| 2006/0003002 A1 | 1/2006 | Fikstad et al. |
| 2006/0034937 A1 | 2/2006 | Patel |
| 2006/0051406 A1 | 3/2006 | Parmar |
| 2006/0106004 A1 | 5/2006 | Brody et al. |
| 2006/0142257 A1 | 6/2006 | Nieschlag |
| 2007/0110777 A1 | 5/2007 | Joabsson et al. |
| 2007/0134336 A1 | 6/2007 | Worle et al. |
| 2007/0154533 A1 | 7/2007 | Dudley |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2008/0317859 A1 | 12/2008 | Sournac et al. |
| 2009/0074859 A1 | 3/2009 | Patel |
| 2010/0136105 A1 | 6/2010 | Chen et al. |
| 2010/0137271 A1 | 6/2010 | Chen et al. |
| 2010/0148675 A1 | 6/2010 | Meijer et al. |
| 2010/0173882 A1 | 7/2010 | Gilivar et al. |
| 2011/0039814 A1 | 2/2011 | Huatan et al. |
| 2011/0142945 A1 | 6/2011 | Chen et al. |
| 2011/0160168 A1 | 6/2011 | Dhingra |
| 2011/0251167 A1* | 10/2011 | Dudley ............... A61K 31/568 514/178 |
| 2011/0263552 A1 | 10/2011 | Dhingra et al. |
| 2012/0135074 A1 | 5/2012 | Giliyar |
| 2012/0148675 A1 | 6/2012 | Chickmath et al. |
| 2012/0244215 A1 | 9/2012 | Giliyar et al. |
| 2012/0322780 A1 | 12/2012 | Giliyar et al. |
| 2013/0022674 A1 | 1/2013 | Dudley et al. |
| 2013/0023505 A1 | 1/2013 | Garfield et al. |
| 2013/0052263 A1 | 2/2013 | Fikstad et al. |
| 2013/0178454 A1 | 7/2013 | Bhasin et al. |
| 2013/0225544 A1 | 8/2013 | Nachaegari et al. |
| 2013/0226644 A1 | 8/2013 | Alonzo et al. |
| 2014/0178466 A1 | 6/2014 | Giliyar et al. |
| 2014/0179652 A1 | 6/2014 | Giliyar et al. |
| 2014/0303130 A1 | 10/2014 | Giliyar et al. |
| 2014/0309202 A1 | 10/2014 | Giliyar |
| 2015/0038475 A1 | 2/2015 | Chickmath et al. |
| 2015/0064243 A1 | 3/2015 | Chen et al. |
| 2015/0273067 A1 | 10/2015 | Patel |
| 2016/0193225 A1 | 7/2016 | Patel |
| 2016/0361322 A1 | 12/2016 | Patel |
| 2016/0367569 A1 | 12/2016 | Giliyar et al. |
| 2017/0056415 A1 | 3/2017 | Patel et al. |
| 2017/0246486 A1 | 8/2017 | Cazier et al. |
| 2018/0125857 A1 | 5/2018 | Giliyar et al. |
| 2018/0228816 A1 | 8/2018 | Giliyar et al. |
| 2018/0228817 A1 | 8/2018 | Gilivar et al. |
| 2018/0243320 A1 | 8/2018 | Giliyar et al. |
| 2018/0333422 A1 | 11/2018 | Chidambaram et al. |
| 2019/0240236 A1 | 8/2019 | Chidambaram et al. |
| 2019/0321374 A1 | 10/2019 | Patel et al. |
| 2019/0350942 A1 | 11/2019 | Patel et al. |
| 2019/0365780 A1 | 12/2019 | Giliyar et al. |
| 2020/0069701 A1 | 3/2020 | Giliyar et al. |
| 2020/0222425 A1 | 7/2020 | Patel et al. |
| 2020/0230152 A1 | 7/2020 | Giliyar et al. |
| 2020/0237781 A1 | 7/2020 | Giliyar et al. |
| 2020/0237782 A1 | 7/2020 | Giliyar et al. |

(56) References Cited

U.S. PATENT DOCUMENTS

| | | |
|---|---|---|
| 2020/0383997 A1 | 12/2020 | Giliyar et al. |
| 2021/0038615 A1 | 2/2021 | Giliyar et al. |
| 2021/0052604 A1 | 2/2021 | Giliyar et al. |
| 2021/0100816 A1 | 4/2021 | Giliyar et al. |
| 2021/0177865 A1 | 6/2021 | Giliyar et al. |

FOREIGN PATENT DOCUMENTS

| | | |
|---|---|---|
| CN | 1346274 A | 4/2002 |
| CN | 101217963 A | 7/2008 |
| DE | 2508615 A1 | 9/1975 |
| DE | 4412464 A1 | 10/1995 |
| DE | 10108614 A1 | 9/2002 |
| EP | 0036145 B1 | 5/1985 |
| EP | 0184942 A2 | 6/1986 |
| EP | 0537070 A1 | 4/1993 |
| EP | 0724877 A1 | 8/1996 |
| EP | 0981328 A1 | 3/2000 |
| EP | 0988858 A1 | 3/2000 |
| EP | 1103252 A1 | 5/2001 |
| EP | 0904064 B1 | 10/2001 |
| EP | 1624855 A2 | 2/2006 |
| EP | 1879456 A1 | 1/2008 |
| EP | 2000130 A1 | 12/2008 |
| EP | 2558073 B1 | 9/2014 |
| FR | 2647346 B1 | 9/1991 |
| FR | 2758459 A1 | 7/1998 |
| GB | 1264677 A | 2/1973 |
| GB | 1567515 | 5/1980 |
| GB | 2098865 A | 12/1982 |
| GB | 2228198 A | 8/1990 |
| JP | S52/66616 A | 6/1977 |
| JP | S52-148060 A | 12/1977 |
| JP | S57/70824 A | 5/1982 |
| JP | H01139526 A | 6/1989 |
| JP | 5194209 A | 8/1993 |
| JP | 07041422 A | 2/1995 |
| JP | H07-508724 A | 9/1995 |
| JP | 09241152 A | 9/1997 |
| JP | 11049664 A | 2/1999 |
| JP | 11152227 A | 6/1999 |
| JP | 2001/500368 A | 1/2001 |
| JP | 2001/508445 A | 6/2001 |
| JP | 2001/514626 A | 9/2001 |
| JP | 2002/510311 A | 4/2002 |
| JP | 2002/520377 A | 7/2002 |
| JP | 2003/500368 A | 1/2003 |
| JP | 2005/500347 A | 1/2005 |
| JP | 2008/537960 A | 10/2008 |
| JP | 2008/540451 A | 11/2008 |
| RU | 2246296 C2 | 2/2005 |
| RU | 2354381 C2 | 5/2009 |
| RU | 2482847 C2 | 5/2013 |
| WO | WO 82/01649 A1 | 5/1982 |
| WO | WO 84/02076 A1 | 6/1984 |
| WO | WO 88/00059 A1 | 1/1988 |
| WO | WO 92/18147 A1 | 10/1992 |
| WO | WO 93/02664 A1 | 2/1993 |
| WO | WO 93/06921 A1 | 4/1993 |
| WO | WO 93/25192 A1 | 12/1993 |
| WO | WO 94/08610 A1 | 4/1994 |
| WO | WO 94/25068 A1 | 11/1994 |
| WO | WO 95/01785 A1 | 1/1995 |
| WO | WO 95/01786 A1 | 1/1995 |
| WO | WO 95/24893 A1 | 9/1995 |
| WO | WO 95/34287 A1 | 12/1995 |
| WO | WO 96/17597 A1 | 6/1996 |
| WO | WO 97/04749 A1 | 2/1997 |
| WO | WO 97/40823 A1 | 11/1997 |
| WO | WO 97/48382 A2 | 12/1997 |
| WO | WO 98/00116 A1 | 1/1998 |
| WO | WO 98/30205 A1 | 7/1998 |
| WO | WO 98/33512 A1 | 8/1998 |
| WO | WO 98/38984 A2 | 9/1998 |
| WO | WO 98/50077 A1 | 11/1998 |
| WO | WO 98/56357 A1 | 12/1998 |
| WO | WO 99/00111 A1 | 1/1999 |
| WO | WO 99/29300 A1 | 6/1999 |
| WO | WO 99/40904 A2 | 8/1999 |
| WO | WO 99/44584 A1 | 9/1999 |
| WO | WO 99/48498 A1 | 9/1999 |
| WO | WO 00/03753 | 1/2000 |
| WO | WO 00/59512 A1 | 10/2000 |
| WO | WO 03/011300 A1 | 2/2003 |
| WO | WO 2004/080383 | 9/2004 |
| WO | WO 2006/113505 A2 | 10/2006 |
| WO | WO 2007/100614 A2 | 9/2007 |
| WO | WO 2010/081032 A2 | 7/2010 |
| WO | WO 2010/102737 A1 | 9/2010 |
| WO | WO 2011/082384 A2 | 7/2011 |
| WO | WO 2011/129812 A1 | 10/2011 |
| WO | WO 2012/101016 A1 | 8/2012 |

OTHER PUBLICATIONS

Addo et al.; "Non Polar Extracts of Serum From Males Contain Covert Radioimmunoassayable Testosterone"; Steroids; (Sep. 1989); pp. 25-269; vol. 54(3).

Alvarez et al.; "The Role of Calcium Ions and Bile Salts on the Pancreatic Lipase-Catalyzed Hydrolysis of Triglyceride Emulsions Stabilized with Lecithin"; Pharmaceutical Research; (1989); pp. 449-457; vol. 6(6).

Andriol® Testocaps®; Consumer Medicine Information; (Sep. 2003).

Androderm® Product Label and Medication Guide; 1995; Labeler—Watson Pharma, Inc.; Revised Nov. 2013; 23 pages.

Androgel® Product Label and Medication Guide; May 2013; Labeler—AbbVie Inc.; Revised Oct. 2013; 28 pages.

Atkinson et al; "Long Term Experience with Testosterone Replacement Through Scrotal Skin; Testosterone: Action, Deficiency and Substitution"; Nieschlag, E. and Behre, HM, Eds.; (1998); pp. 365-388.

Aungst; "Intestinal Permeation Enhancers," Journal of Pharmaceutical Sciences; (2000); pp. 429-442; vol. 89(4).

Baert et al.; "Analytical, biopharmaceutical and regulatory evaluation of topical testosterone preparations"; European Journal of Pharmaceutics and Biopharmaceutics; (2009); pp. 275-281; vol. 72; <doi: 10.1016/j.ejpb.2008.10.014 >.

Bagchus et al.; "Important Effect of Food on the Bioavailability of Oral Testosterone Undecanoate"; Pharmacotherapy: (2003); pp. 319-325; vol. 23(3).

Baluom et al.; "The Importance of Intestinal Residence Time of Absorption Enhancer on Drug Implication on Formulative Considerations"; International Journal of Pharmaceutics; (1998); pp. 21-30; vol. 176.

Bates et al.; "Bioavailability of Micronized Griseofulvin from Corn Oil-in-Water Emulsion, Aqueous Suspension, and Commercial Tablet Dosage Forms in Humans"; Journal of Pharmaceutical Sciences; (1975); pp. 793-797; vol. 64(5).

Beatch et al.; "Ventricular Fibrillation, an Uncontrolled Arrhythmia Seeking New Targets"; Drug Development Research Journal; (2002); pp. 45-52; vol. 55.

Bernkop-Schnurch; "The Use of Inhibitory Agents to Overcome the Enzymatic Barrier to Orally Administered Therapeutic Peptides and Proteins"; Journal of Controlled Release; (Apr. 1998); pp. 1-16; vol. 52(1-2).

Bhargava et al.; "Using Microemulsions for Drug Delivery"; Pharmaceutical Technology; (Mar. 1987); pp. 46-53.

Blystone et al.; "Toxicity and Carcinogenicity of Androstenedione in F344/N Rats and B6C3F2 Mice"; Food and Chemical Toxicology; (Sep. 2011); pp. 2116-2124; <doi: 10.1016/j.fct.2011.05.026. Epub2011May30 >.

Bugay; "Characterization of the Solid-State: Spectroscopic Techniques"; Advanced Drug Delivery Review; (May 16, 2001); pp. 43-65; vol. 48(1).

Burbello et al.; Sovremennye Lekarstvennyesredstava S-Pb Neva; (2004); p. 567.

Cantrill; "Which Testosterone Replacement Therapy"; Clinical Endocrinology Journal; (1984); pp. 97-107; vol. 21.

(56) References Cited

OTHER PUBLICATIONS

Charman et al.; "Physicochemical and Physiological Mechanisms for the Effects of Food on Drug Absorption: The Role of Lipids and pH"; Journal of Pharmaceutical Sciences; (1997); pp. 269-282; vol. 86(3).
Constantidides; "Lipid Microemulsion for Improving Drug Dissolution and Oral Absorption: Physical and Biopharmaceutical Aspect"; Pharmaceutical Research; (1995); pp. 1561-1572; vol. 12(11).
Depo-Testosterone® Product Label and Medication Guide; Sep. 2006; Labeler—Pharmacia & Upjohn Company; Revised Aug. 2013; 12 pages.
Emulsion; IUPAC Compendium of Chemical Terminology, 2nd Ed., 1997.
Frey et al.; "Bioavailability of Oral Testosterone in Males"; European Journal of Pharmacology; (1979); pp. 345-349; vol. 16.
Gennaro; "Surfactant Properties in Solution and Micelle Formation, Colloidal Dispersions"; Remington's Pharmaceutical Sciences; (1985); pp. 293-300; Chapter 20.
Goncharova et al.; "Preparation of Testosterone Esters"; Pharmaceutical Chemistry Journal; (Jul. 1973); pp. 427-428; vol. 7(7).
Gonzalo-Lumbrerars et al.; "HPLC Method Development for Testosterone Propionate and Cipionate in Oil-Based Injectables"; Journal of Pharmaceutical and Biomedical Analysis; (Jul. 15, 2005); pp. 757-762; vol. 38(4).
Gooren; "A Ten-year Safety Study of the Oral Androgen Testosterone Undecanoate"; Journal of Andrology: (1994); pp. 212-215; vol. 15(3).
Grahame-Smith et al; The Oxford Textbook of Clinical Pharmacology and Drug Therapy; (1992); pp. 25, 136-137; $2^{nd}$ Edition; M. Meditsina Publishers; (English version included pp. 9-12, 122-124).
Healthline; "What are the symptoms of Hypogonadism?"; 1 page; [Internet]; [Retrieved on Apr. 1, 2014] [Retrieved from <URL: http://www.healthline.com/health/hypogonadism#Overview1 >].
Hong, B.S., et al.; "Recent trends in the treatment of testosterone deficiency syndrome"; International Journal of Urology; (2007); pp. 981-985; vol. 14; The Japanese Urological Association; <doi: 10.1111/j.1442-2042.2007.01882.x >.
Hörter et al.; "Influence of Physiochemical Properties on Dissolution of Drugs in the Gastrointestinal Tract"; Advanced Drug Delivery Reviews; (1997); pp. 3-14; vol. 25.
Houwing et al.; "Pharmacokinetic Study in Women of Three Different Doses of a New Formulation of Oral Testosterone Undecanoate, Andriol Testocaps", Pharmacotherapy; (2003); pp. 1257-1265; vol. 23(10).
Humberstone et al.; "Lipid-based Vehicles for the Oral Delivery of Poorly Water Soluble Drugs"; Advanced Drug Delivery Reviews; (1997) pp. 103-128.
Hutchison; "Digestible Emulsions and Microemulsions for Optimum Oral Delivery of Hydrophobic Drugs"; Bulletin Technique Gattefosse; (1994); pp. 67-74; vol. 87.
Javanbakht et al; "Pharmacokinetics of a Novel Testosterone Matrix Transdermal System In Health, Premenopausal Women and Women Infected with the Human Immunodeficiency Virus 1"; Journal of Clinical Endocrinology & Metabolism; (2000); pp. 2395-2401; vol. 85(7).
Johnson; "Gastrointestinal Physiology"; Department of Physiology; University of Texas Medical School: (1997); pp. 25-26, 93-106, 133-134, 136-137; Houston, Texas.
Julien; "A concise nontechnical guide to the actions, uses, and side effects of psychoactive drugs"; A Primer of Drug Action; (2001); pp. 5-6; $9^{th}$ Edition.
Kalinchenko; "Testosterone—King Hormones, hormones kings"; The Journal; Sex and Life; (2004); pp. 12-22; [Retrieved on Mar. 26, 2010]; [Retrieved from <URL: http://www.laz.med.ru/interesting/publications/testosterone.html >].
Köhn et al.; "A New Oral Testosterone Undecanoate Formulation"; World Journal of Urology; (Nov. 2003); pp. 311-315; vol. 21(5); <doi: 10.1007/s00345-003-0372-x>.
Langer; "New Methods of Drug Delivery"; Science; (Sep. 1990); pp. 1527-1533; vol. 249(4976).

Lecluyse et al.; "In Vitro Models for Selection of Development Candidates. Permeability Studies to Define Mechanisms of Absorption Enhancement"; Advanced Drug Delivery Reviews; (1997); pp. 163-183; vol. 23.
Leichtnam et al.; "Testosterone Hormone Replacement Therapy: State-of-the-Art and Emerging Technology"; Pharmaceutical Research; (2006); pp. 1117-1132; vol. 23(6).
LGC: Reference Standard Testosterone Undecanoate; Certificate of Analysis; (Jul. 5, 2015); 6 pages; LGC GmBH; Germany.
Lopez-Berestein et al. (Eds.); Liposomes in the Therapy of Infectious Disease and Cancer; (1989); pp. 353-365; Liss; New York.
MacGregor et al.; "Influence of Lipolysis on Drug Absorption From the Gastro-Intestinal Tract"; Advanced Drug Delivery Reviews; (1997); pp. 33-46; vol. 25.
Maisey et al; "Clinical Efficacy of Testosterone Undecanoate in Male Hypogonadism"; Clinical Endocrinology; (1981); pp. 625-629; vol. 14.
McAuley et al; "Oral Administration of Micronized Progesterone: A Review and More Experience"; Pharmacotherapy; (May 1996); pp. 453-457; vol. 16(3).
Meinert et al.; Clinical Trials: Design, Conduct and Analysis (Monographs in Epidemiology and Biostatistics; (1986); vol. 8.
Merck Index, "Alpha Tocopherol"; Monograph 09571; (2001-2004); Merck & Co. Inc.
Merck Index; "Amiodarone"; Monograph 504; (1996); p. 84; $12^{th}$ Edition; Merck & Co., Inc.
Merck Index; "Carvedilo"; Monograph 01888; (2001-2004); Merck & Co., Inc.
Merck Index; "Fenofibrate"; Monograph 3978; (2006); pp. 679-680; $14^{th}$ Edition; Merck & Co., Inc.
Merck Index; "Risperidone"; Monograph 08316; (2001-2004); Merck & Co., Inc.
Merck Index; "Shellac"; Monograph 8623; (1996); p. 8526; $12^{th}$ Edition.
Merck Index; "Testosterone"; Monograph 9322; (1996); p. 9326; $12^{th}$ Edition; Merck & Co., Inc.
Merck Index; "Vitamin E" and "Vitamin E Acetate"; Monographs 9931 and 9932; (1989); pp. 1579-1580; $11^{th}$ Edition; Merck & Co., Inc.
Merck Index; "Vitamin E"; Monograph 10021; (2006); p. 1726; $14^{th}$ Edition; Merck & Co., Inc.
Merck Index; "Ziprasidone"; Monograph 10224;(2001-2004); Merck & Co., Inc.
Merriam-Webster Dictionary; "Granule"; [Retrieved Dec. 17, 2009] [Retrieved from <URL: http://www.mw.com/dictionary/granule >].
Mittal et al; "The Wide World of Micelles"; In: International symposium on Micellization, Solubilization, and Microemulsions, $7^{th}$ Northeastern Regional Meeting of the American Society; Albany, New York; (1976); pp. 1-21; vol. 1 <ISBN: 0-306-31023-6(v.1) >.
Moellering; "Vancomycin: A 50-Year Reassessment"; Clinical Infectious Diseases; (2006); pp. S3-S4; vol. 42.
Muranishi; "Absorption Enhancers"; Critical Reviews in Therapeutic Drug Carrier Systems; (1990); pp. 1-33; vol. 7(1).
Muranishi; "Potential Absorption of Heparin from the Small Intestine and the Large Intestine in the Presence of Monoolein Mixed Micelles"; Chemical and Pharmaceutical Bulletin Journal; (1977); pp. 1159-1161; vol. 24(5).
Nieschlag et al.; "Plasma Androgen Levels in Men after Oral Administration of Testosterone or Testosterone Undecanoate"; Acta Endocrinologica; (1975); pp. 366-374; vol. 79(2); (Abstract).
Noguchi et al; "The Effect of Drug Lipophilicity and Lipid Vehicles on the Lymphatic Absorption of Various Testosterone Esters"; International Journal of Pharmaceutics; (May 1985); pp. 173-184; vol. 24(2-3).
Osol (Ed.); "Emulsions"; Remington's Pharmaceutical Sciences; (1975); pp. 327-339, 1452-1456; $15^{th}$ Edition.
Pechersky et al.; "The Effects of Changes in Testosterone Level on the Development of Prostate Cancer;" Urology; (Sep. 2005); pp. 14-15; vol. 66, (Supplement 3A); 37.
Pechersky et al. "Androgen administration in middle-aged and aging men: effects of oral testosterone undecanoate on dihydrotestosterone, oestradiol and prostate volume"; International Journal of Andrology; (2002); pp. 119-125; vol. 25.

(56) References Cited

OTHER PUBLICATIONS

Pfeil et al.; "Current and Future Testosterone Delivery Systems for Treatment of the Hypogonadal Male;" Expert Opinion on Drug Delivery; (Apr. 21, 2008); pp. 471-481; vol. 5, No. 4; <doi: 10-1517/17425247.5.4.471 >.
Pouton; "Formulation of Self-Emulsifying Drug Delivery Systems"; Advanced Drug Delivery Reviews; (1997); pp. 47-58; vol. 25.
Pozo et al.; "Quantification of Testosterone Undecanoate in Human Hair by Liquid Chromatography-Tandem Mass Spectrometry"; Biomedical Chromatography; (Aug. 2009); pp. 873-880; vol. 23(8).
Remington; "Surfactant Properties in Solution and Micelle Formation"; The Science and Practice of Pharmacy; (1995); pp. 272-276; (19th Edition).
Reymond et al.; "In Vivo Model for Ciclosporin Intestinal Absorption in Lipid Vehicles"; Pharmaceutical Research; (1988); pp. 677-679; vol. 5(10).
S1 SEC Filing (Securities and Exchange Commission) for Clarus Therapeutics, Inc.; Filed May 23, 2014 with the Securities and Exchange Commission; 207 pages.
Saudek et al.; "A preliminary trial of the programmable implantable medication system for insulin delivery"; The New England Journal of Medicine; (Aug. 31, 1989); pp. 574-579; vol. 321.
Schnabel et al.; "The effect of food composition on serum testosterone levels after oral administration of Andriol Testocaps"; Clinical Endocrinology; (2007); pp. 579-585; vol. 66(4).
Schott; "Comments on Hydrophile-Lipophile Balance Systems"; Journal of Pharmaceutical Sciences; (Jan. 1990); pp. 87-88; vol. 79(1); American Pharmaceutical Association.
sciencelab.com; "MSDS: Glyceryl Monooleate"; Material Safety Data Sheet; (Oct. 2005); 5 pages; <URL: www.sciencelab.com >.
Sefton; "Implantable Pumps"; Critical Reviews in Biomedical Engineering; (1987); pp. 201-240; vol. 14, No. 3; (Abstract); [Sourcelink] <URL: http://www.ncbi.nlm.nih.gov/pubmed/3297487 >.
Seidman et al.; "Testosterone replacement therapy for hypogonadal men with SSRI-refractory depression"; Journal of Affective Disorders; (1998); pp. 157-161; vol. 48.
Shackleford et al., "Contribution of Lymphatically Transported Testosterone Undecanoate to the Systemic Exposure of Testosterone after Oral Administration of two Andriol Formulations in Conscious Lymph Duct-Cannulated Dogs"; The Journal of Pharmacology and Experimental Therapeutics; (2003); pp. 925-933; vol. 306(3).
Shanghai PI Chemicals Ltd.; "MSDS: Testosterone Undecanoate"; Material Safety Data Sheet; (2007); [Retrieved on Jun. 3, 2009] [retrieved from <URL: http://www.pipharm.com/product/msds-13457.pdf >].
Stedman's Medical Dictionary; "Dehydro-e-epiandrosterone"; "Dehydroisoandroteron"; and "Steriod"; (1972); pp. 329, 1195-1197; 22nd Edition; Williams & Wilkins Co.
Stedman's Medical Dictionary; "Hydroxy-Acid and Vitamin E"; (1973); pp. 595, 14000; 22nd Edition; Williams & Wilkins Co.
Stedman's Medical Dictionary; "Surfactants"; (1972); p. 1225; 22nd Edition; Williams & Wilkins Co.
Stedman's Medical Dictionary; "Surfactants"; (2006); 28nd) Edition; Williams & Wilkins Co.
Swerdloff, et al; "Long Term pharmaceokinetics of transdermal testosterone gel in hypogonadal men". Journal of Clinical Endocrinology & Metabolism; (2000); pp. 4500-4510; vol. 85.
Tarr et al.; "Enhanced Intestinal Absorption of Cyclosporine in Rats Through the Reduction of Emulsion Droplet Size"; Pharmaceutical Research; (1989); pp. 40-43; vol. 6(1).
Tarumi et al.; "Androstenedione induces abnormalities in morphology and function of developing oocytes, which impairs oocyte meiotic competence"; Journal of Fertility and Sterility; (Feb. 2012); pp. 469-476; vol. 97(2); <doi: 10.1016/j.fertnstert.2011.11.040 >.
Tauber et al.; "Absolute bioavailability of testosterone after oral administration of testosterone-undecanoate and testosterone"; European Journal of Drug Metabolism and Pharmacokinetics; (1986); pp. 145-149; vol. 11(2); [Sourcelink] <URL: http://www.ncbi.nlm.nih.gov/pubmed/3770015 >; [Abstract].
Temina et al.; "Diversity of the fatty acids of the Nostoc species and their statistical analysis"; Microbiological Research; (2007); pp. 308-321; Elsevier GmbH.
Tenover; "The Androgen-Deficient Aging Male: Current Treatment Options"; Reviews in Urology; (2003); pp. S22-S28; vol. 5, Suppl. 1.
Testim® Product Label and Medication Guide; (Sep. 2009); Labeler—A-S Medications Solutions LLC; Revised Jun. 2013; 17 pages.
Torpac® Inc.; "Capsule Size Chart, Metric Table and English Table"; (2000); 3 pages; Torpac Inc., Fairfield, New Jersey; [Internet] [retrieved on Sep. 2014] [retrieved from <URL: www.torpac.com >].
Treat et al.; "Liposome Encapsulated Doxorubicin preliminary result of Phase I and Phase II Trials"; Liposomes in the Therapy of Infectious Diseases and Cancer; Lopez-Berestein and Fidler (Eds.); (1989); pp. 353-365; Liss, New York.
Tso, et al; "Intestinal Absorption and Lymphatic Transport of a High γ-Linolenic Acid Canola Oil in Lymph Fistula Sprague-Dawley Rats"; The Journal of Nutrition; (2002); pp. 218-221; American Society for Nutritional Sciences.
Wang, et al; "Long-term testosterone gel (AndroGel®) Treatment Maintains Beneficial Effects on Sexual Function and Mood, Lean and Fat Mass and Bone Mineral Density in Hypogonadal Men"; Journal of Clinical Endocrinology & Metabolism; (2004); pp. 2085-2098; vol. 89.
Webster et al.; "Validation of Pharmaceutical Potency Determinations by Quantitative Nuclear Magnetic Resonance Spectrometry"; Journal of Applied Spectroscopy; (May 2010); pp. 537-542; vol. 64(5).
Wilson et al.; "The Behaviour of Fats and Oils in the Upper G.I. Tract"; Bulletin Technique Gattefosse; (1997); pp. 13-18; vol. 90.
Winne; "Dependence of Intestinal Absorption in Vivo on the Unstirred Layer"; Archives of Pharmacology; (1978); pp. 175-181; vol. 304.
Yassin et al.; "Long-acting testosterone undecanoate for parenteral testosterone therapy"; Therapy, Future Drugs; (2006); pp. 709-721; vol. 3(6).
Yin et al., "Dietary Fat Modulates the Testosterone Pharmacokinetics of a New Self-Emulsifying Formulation of Oral Testosterone Undecanoate in Hypogonadal Men"; Journal of Andrology; (Nov./Dec. 2012); pp. 1282-1290; vol. 33(6).
Yin et al.; "Reexamination of Pharmacokinetics of Oral Testosterone Undecanoate in Hypogonadal Men with a New Self-Emulsifying Formulation"; Journal of Andrology; (2012); pp. 190-201; vol. 33(2).
Zhi et al.;"Effects of dietary fat on drug absorption"; Clinical Pharmacology & Therapeutics; (Nov. 1995); pp. 487-491; vol. 58(5).
Andriol® Testocaps®; "Testosterone Undecanoate;" Consumer Medicine Information; [Insert]; (Jul. 2011); 3 pages.
Somsen et al.; "Coupling of LC and FT-IR: Impurity Profiling of Testosterone Undecanoate;" Applied Spectroscopy; 46; 10; 1992, pp. 1514-1519.

* cited by examiner

COMPOSITION AND METHOD FOR ORAL DELIVERY OF ANDROGEN PRODRUGS

PRIORITY DATA

This application is a continuation of U.S. patent application Ser. No. 15/861,492, filed Jan. 3, 2018, which is a continuation of U.S. patent application Ser. No. 15/183,691, filed Jun. 15, 2016, which claims the benefit of U.S. Provisional Application No. 62/175,931 filed Jun. 15, 2015 and U.S. Provisional Application No. 62/253,292 filed Nov. 10, 2015, each of which is incorporated by reference in their entireties.

FIELD OF THE INVENTION

Described herein are methods of treatment with pharmaceutical compositions and dosage forms. Accordingly, the present disclosure generally involves health sciences, the fields of chemistry, pharmaceutical sciences, and medicine.

BACKGROUND OF THE INVENTION

A particularly difficult problem in regards to orally administered lipophilic drugs is pharmacokinetic variability seen based on food effects. Many pharmaceuticals have important dosing requirements based on the effect of food on their pharmacokinetics. Some pharmaceuticals need to be taken without food. Some pharmaceuticals need to be taken with food. Other pharmaceuticals need to be taken with specific types of food. Yet other pharmaceuticals can be taken regardless of food. More complicated or specific food requirements for dosing can lead to less than desirable efficacy or safety of the pharmaceutical since; in general, a target population has quite variable eating habits. For instance, certain people are vegetarians, certain people may not eat breakfast, certain people may have a low-fat diet, certain people may have a high-fat diet, and certain people have highly variable diets with respect to fat content. These variables are difficult to control in a real world setting. Studies with Andriol Testocaps®, a testosterone undecanoate containing oral product, have shown that meal fat content has substantial effects on the bioavailability of serum testosterone. Schnabel et al., Clinical Endocrinology (2007) 66, 579-585. Similarly, another testosterone undecanoate oral formulation being developed by Clams Therapeutics exhibits non-bioequivalency as a function of meal fat content. See Yin et al. J Androl. 2012 November-December; 33(6): 1282-1290).

Thus, the present inventors recognize a need for oral formulations with testosterone undecanoate bioavailability that is not substantially altered by meal fat content.

SUMMARY OF THE INVENTION

The present disclosure is related to formulations and methods of orally administering formulations containing a lipophilic drug such as testosterone undecanoate ("TU") or other testosterone esters.

The present inventors have surprisingly discovered oral testosterone undecanoate compositions that can be effectively administered to hypogonadal males with a meal without the fat content of the meal substantially effecting bioavailability. This result is unexpected and in direct contrast to the bioavailability performance reported for many other testosterone undecanoate oral formulations, which conclude that bioavailability is affected by meal fat content.

Upon receipt of the information in this disclosure, the ordinarily skilled artisan will be able to recognize oral testosterone undecanoate formulations that are bioequivalent to the formulations disclosed herein, including formulations that are bioequivalent for $C_{max}$, $AUC_{(0-t)}$, $AUC_{(0-\infty)}$, $C_{avg}$, or a combination thereof at low, standard, and high fat conditions as well as standard versus low fat, standard versus high fat and low versus high fat for serum testosterone, testosterone undecanoate, dihydrotestosterone, dihydrotestosterone undecanoate, or a combination thereof. Pharmaceutically equivalent formulations are also provided.

In view of the results described herein, a pharmaceutical composition is provided that is bioequivalent for serum testosterone, testosterone undecanoate, dihydrotestosterone, dihydrotestosterone undecanoate or a combination thereof for $C_{max}$, $AUC_{(0-t)}$, $AUC_{(0-\infty)}$, $C_{avg}$, or a combination thereof for a standard meal versus either a low fat or high fat meal; for low, standard, and high fat meals; for low versus high fat. The pharmaceutical compositions or dosage forms can also be pharmaceutically equivalent.

Described herein are pharmaceutical compositions that are bioequivalent for serum testosterone levels to a formulation having 50 mg to 350 mg testosterone undecanoate (e.g., in one aspect either 75 mg or 112.5 mg TU) at about 15 wt % loading, about 63 wt % Maisine 35-1, about 16 wt % Cremophor RH 40 and about 6 wt % PEG 8000. The bioequivalent composition typically has from 10 wt %-50 wt % testosterone undecanoate and 50 wt %-90 wt % pharmaceutically acceptable carrier. The bioequivalent compositions are bioequivalent for serum testosterone undecanoate, dihydrotestosterone, dihydrotestosterone undecanoate, or a combination thereof for $C_{max}$, $AUC_{(0-t)}$, $AUC_{(0-\infty)}$, $C_{avg}$, or a combination thereof at low, standard, and high fat conditions as well as standard versus low fat, standard versus high fat and low versus high fat. Any carrier can be used so long as the compositions are bioequivalent to the formulation having 50 mg to 350 mg testosterone undecanoate (e.g., in one aspect either 75 mg or 112.5 mg TU) at about 15 wt % loading, about 63 wt % Maisine 35-1, about 16 wt % Cremophor RH 40 and about 6 wt % PEG 8000. In some aspects, the formulation is also pharmaceutically equivalent to that described herein.

Also provided herein are methods for replacement therapy in a male for conditions associated with a deficiency or absence of endogenous testosterone. The methods involve orally administering a pharmaceutical composition having TU and a pharmaceutically acceptable carrier with a meal. The meal can be any meal regardless of fat content, the meal can also be a low fat meal, a standard fat meal, or a high fat meal. The methods provide bioequivalent $C_{max}$, $AUC_{(0-t)}$, $AUC_{(0-\infty)}$, $C_{avg}$, or a combination thereof, when administered with any of low fat, standard fat, or high fat meals. Alternatively, the methods provide bioequivalent $C_{max}$, $AUC_{(0-t)}$, $AUC_{(0-\infty)}$, $C_{avg}$, or a combination thereof, when administered with a standard fat meal as compared to low or high fat meals. In another alternative, the method provides bioequivalent $C_{max}$, $AUC_{(0-t)}$, $AUC_{(0-\infty)}$, $C_{avg}$, or a combination thereof when administered with a low fat meal as compared to a high fat meal. When the composition is administered with a TU total daily dose range of about 275 mg (e.g., 300 mg) to about 625 mg (e.g., 600 mg), the composition provides a serum testosterone $C_{avg}$ at steady state in the range of 300 ng/dL to about 1100 ng/dL to a subject in need of treatment. The methods can include a dose titration as described herein.

Thus, the results described herein support a drug label indicating (or method involving) that the oral testosterone replacement therapy (testosterone undecanoate containing oral dosage form) is taken (1) "WITH A MEAL" or (2) "WITH MEAL, BUT NOT ON EMPTY STOMACH" or (3) "WITH FAT CONTAINING FOOD" not specifying fat content. In an alternative, the drug label may indicate (or method may involve) the oral testosterone replacement therapy (testosterone undecanoate containing oral dosage form) is taken "WITH MEAL, BUT NOT LOW FAT". In an alternative, the drug label may indicate (or method may involve) the oral testosterone replacement therapy (testosterone undecanoate containing oral dosage form) is taken "WITH MEAL, BUT NOT HIGH FAT". In an alternative, the drug label may indicate (or method may involve) the oral testosterone replacement therapy (testosterone undecanoate containing oral dosage form) is taken "WITH STANDARD OR NORMAL MEAL".

DETAILED DESCRIPTION

Before the present testosterone undecanoate compositions, oral dosage forms, such as capsules, and related methods of use are disclosed and described in more detail and variations, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

In specific embodiments, provided herein are the following:

(1) A method for replacement therapy in a male for conditions associated with a deficiency or absence of endogenous testosterone, said method comprising: orally administering to a male having a condition associated with a deficiency or absence of endogenous testosterone, with a meal, a pharmaceutical composition comprising from about 50 mg to about 300 mg of testosterone undecanoate and a pharmaceutically acceptable carrier said pharmaceutical acceptable carrier being selected to provide bioequivalent amounts of serum testosterone, testosterone undecanoate, dihydrotestosterone or dihydrotestosterone undecanoate levels to said male for (i) meals containing standard fat as compared to low fat and high fat, (ii) for meals containing low fat as compared to high fat, or both (i) and (ii).

(2) The method as in 1, said pharmaceutical composition having about 75 mg, about 112.5 mg, about 150 mg, about 225 mg, or about 300 mg of testosterone undecanoate.

(3) The method as in 1, said pharmaceutical acceptable carrier selected to provide bioequivalent amounts of serum testosterone levels to said male for meals containing low fat, standard fat and high fat.

(4) The method as in 1, said method providing a serum testosterone $C_{avg}$ in the range of 300 ng/dL to 1100 ng/dL.

(5) The method as in 1, wherein said administering is twice-a-day.

(6) The method as in 1, said method comprising administering from 285 mg to about 625 mg of testosterone undecanoate per day.

(7) The method as in 1, said composition comprising a lipophilic additive.

(8) The method as in 1, said composition comprising a hydrophilic additive.

(9) The method as in 1, said pharmaceutical composition (i) being pharmaceutically equivalent to an oral pharmaceutical composition having about 75 mg or about 112.5 mg of testosterone undecanoate at about 15 wt % loading, about 63 wt % Maisine 35-1 (glyceryl monolinoleate), about 16 wt % Cremophor RH 40 (Polyoxyl 40 hydrogenated castor oil) and about 6 wt % PEG 8000 (polyethylene glycol having an average molecular weight of 8,000 grams/mole) or (ii) has about 75 mg or about 112.5 mg of testosterone undecanoate at about 15 wt % loading, about 63 wt % Maisine 35-1, about 16 wt % Cremophor RH 40 and about 6 wt % PEG 8000.

(10) The method as in 1, said method comprising administering the pharmaceutical composition as 2, 3, 4, 5, 6, 7, or 8 unit dosage forms per day.

(11) A method for replacement therapy in a male for conditions associated with a deficiency or absence of endogenous testosterone, said method comprising: orally administering to a male having a condition associated with a deficiency or absence of endogenous testosterone, with a meal having about 10 wt % to 50 wt % fat, a pharmaceutical composition comprising from about 50 mg to about 300 mg of testosterone undecanoate and a pharmaceutically acceptable carrier said pharmaceutical acceptable carrier is selected to provide bioequivalent amounts of serum testosterone, testosterone undecanoate, dihydrotestosterone or dihydrotestosterone undecanoate levels to said male for meals containing (i) standard fat as compared to low fat and high fat, (ii) low fat to high fat or (iii) a combination thereof.

(12) The method as in 11, said pharmaceutical composition (i) being pharmaceutically equivalent to an oral pharmaceutical composition having about 75 mg or about 112.5 mg of testosterone undecanoate at about 15 wt % loading, about 63 wt % Maisine 35-1, about 16 wt % Cremophor RH 40 and about 6 wt % PEG 8000 or (ii) has about 75 mg or about 112.5 mg of testosterone undecanoate at about 15 wt % loading, about 63 wt % Maisine 35-1, about 16 wt % Cremophor RH 40 and about 6 wt % PEG 8000.

(13) The method as in 11, said method providing a serum testosterone Cavg in the range of 300 ng/dL to 1100 ng/dL.

(14) The method as in 11, said method comprising administering from 285 mg to about 625 mg of testosterone undecanoate per day.

(15) The method as in 11, wherein said administering is twice-a-day.

(16) A pharmaceutical composition for oral administration comprising testosterone undecanoate and a pharmaceutical acceptable carrier said pharmaceutical composition providing bioequivalent amounts of serum testosterone undecanoate, testosterone, dihydrotestosterone, dihydrotestosterone undecanoate or a combination thereof to a male for conditions associated with a deficiency or absence of endogenous testosterone when administered with a meal (i) containing medium fat as compared to high fat or low fat or (ii) containing low, standard, or high fat.

(17) The pharmaceutical composition as in 16, said pharmaceutical composition being pharmaceutical equivalent to an oral pharmaceutical composition having about 75 mg or about 112.5 mg of testosterone undecanoate at 15 wt % loading, 63 wt % Maisine 35-1, 16 wt % Cremophor RH 40, and 6 wt % PEG 8000.

(18) The pharmaceutical composition as in 16 comprising a monoglyceride, a diglyceride or a combination thereof in amount of greater than about 10 wt % and has less than about 50 wt % triglyceride.

(19) A pharmaceutical composition for oral administration that is hypogonadal male serum testosterone bioequivalent to a formulation comprising 15 wt % testosterone undecanoate, about 63 wt % Maisine 35-1, about 16 wt % Cremophor RH 40, and about 6 wt % polyethylene glycol 8000 under medium fat as compared to low fat and high fat with the proviso that the formulation does not comprises about 15 wt % testosterone undecanoate, about 63 wt % Maisine 35-1, about 16 wt % Cremophor RH 40, and about 6 wt % polyethylene glycol 8000.

(20) The pharmaceutical composition as in 19, said pharmaceutical composition being pharmaceutically equivalent to an oral pharmaceutical composition having about 75 mg or about 112.5 mg of testosterone undecanoate at 15 wt % loading, 63 wt % Maisine 35-1, 16 wt % Cremophor RH 40, and 6 wt % PEG 8000.

(21) The pharmaceutical composition as in 19, comprising a monoglyceride, a diglyceride or a combination thereof in amount of greater than 10 wt % and has less than 50 wt % triglyceride.

(22) A pharmaceutical composition for oral administration for replacement therapy in a male for conditions associated with a deficiency or absence of endogenous testosterone comprising testosterone undecanoate and a pharmaceutical acceptable carrier said pharmaceutical composition indicated to be taken (i) "WITH A MEAL", (ii) "WITH MEAL, BUT NOT ON EMPTY STOMACH", (iii) "WITH FAT CONTAINING FOOD" not specifying fat content, (iv) "WITH MEAL, BUT NOT LOW FAT", (v) "WITH MEAL, BUT NOT HIGH FAT", or (vi) "WITH STANDARD OR NORMAL MEAL".

(23) The pharmaceutical composition as in 22, said pharmaceutical composition indicated to be taken "WITH A MEAL".

(24) The pharmaceutical composition as in 22, said pharmaceutical composition indicated to be taken "WITH MEAL, BUT NOT ON EMPTY STOMACH".

(25) The pharmaceutical composition as in 22, said pharmaceutical composition indicated to be taken "WITH FAT CONTAINING FOOD" not specifying fat content.

(26) The pharmaceutical composition as in 22, said pharmaceutical composition indicated to be taken "WITH MEAL, BUT NOT LOW FAT".

(27) The pharmaceutical composition as in 22, said pharmaceutical composition indicated to be taken "WITH MEAL, BUT NOT HIGH FAT".

(28) The pharmaceutical composition as in 22, said pharmaceutical composition indicated to be taken "WITH STANDARD OR NORMAL MEAL"

(29) The method of any one of 1-15 further comprising a dose titration of testosterone undecanoate.

(30) The method of any one of 1-15 or 29 with a pharmaceutical composition as in any one of 16-29 to the extent the methods and compositions are not inconsistent with one another.

(31) The pharmaceutical composition of any one of claims 16-28 disposed or contained in a capsule. (32) The pharmaceutical composition as in 22, indicated to be taken with a meal having at least 10 grams or about 10 grams of fat.

(33) The pharmaceutical composition as in 22, indicated to be taken with a meal having at least 15 grams or about 15 grams of fat.

(34) An oral dosage form in a container that includes a container having a label and an oral dosage form contained within the container. The oral dosage form can include testosterone undecanoate and a pharmaceutically acceptable carrier. The label on the container can indicate that the oral dosage form is to be taken (1) "WITH A MEAL", (2) "WITH MEAL, BUT NOT ON EMPTY STOMACH", (3) "WITH FAT CONTAINING FOOD" not specifying fat content, (4) "WITH MEAL, BUT NOT LOW FAT", (5) "WITH MEAL, BUT NOT HIGH FAT", or (6) "WITH STANDARD OR NORMAL MEAL".

(35) The oral dosage form as in 34, wherein the container is selected from a bottle, a pouch, or a blister package.

It should be noted that as used in this written description, the singular forms "a," "an," and, "the" include express support for plural referents unless the context clearly dictates otherwise. Thus, for example, reference to "an excipient" includes support for one or more of such excipients, and reference to "the carrier" includes support for one or more of such carriers.

Definitions

As used herein, "pharmaceutically equivalent", refers to a composition or unit dosage form drug product if they meet three criteria: they contain the same active ingredient(s); they are of the same dosage form and route of administration; they are identical in strength or concentration. Typically, pharmaceutical equivalent drug products may differ in characteristics such as shape, release mechanism, labeling (to some extent), scoring and excipients (including colors, flavors, preservatives) although this list in not-limiting.

As used herein, "bioequivalent", refers to the absence of a significant difference in the rate and extent to which the active ingredient or active moiety in pharmaceutical equivalents or pharmaceutical alternatives becomes available at the site of drug action when administered at the same dose under similar conditions in an appropriately designed study. Two products are bioequivalent if the 90% CI (Confidence Interval) of the relative mean $C_{max}$, $AUC_{(0-t)}$ and $AUC_{(0-\infty)}$ of the test (e.g., generic formulation) to reference (e.g., innovator brand formulation) should be within 70% to 143% and preferably 80.00% to 125.00% under particular conditions e.g., fed, fasted, particular fat content in meals (e.g., low, standard, or high). Unless otherwise specified, bioequivalence can be for serum testosterone undecanoate, serum testosterone, serum dihydrotestosterone or serum dihydrotestosterone undecanoate. Typically, bioequivalence is determined with a group of subjects.

As used herein, the term "treatment," when used in conjunction with the administration of pharmaceutical compositions and oral dosage capsules containing testosterone undecanoate, refers to the administration of the oral dosage capsules and pharmaceutically acceptable composition to subjects who are either asymptomatic or symptomatic. In other words, "treatment" can both be to reduce or eliminate symptoms associated with a condition present in a subject, or it can be prophylactic treatment, i.e., to prevent the occurrence of the symptoms in a subject. Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

As used herein, the term "fatty acid" refers to unionized carboxylic acids with a long aliphatic tail (chain), either saturated or unsaturated, conjugated or non-conjugated. Typically, the fatty acid is a $C_8$ to $C_{22}$ fatty acid.

Unless otherwise specified, the term $C_8$ to $C_{22}$ fatty acid glycerides refers to a mixture of mono-, di-, and/or triglycerol esters of medium to long chain ($C_8$ to $C_{22}$) fatty acids.

As used herein, the term "solidifying agent" or "solidifying additive" are used interchangeably and refer to a pharmaceutically acceptable additive that is in a solid physical state at 20° C. Similarly, a "solid lipophilic additive" refers to a lipophilic compound or component that is in a solid physical state at 20° C. and/or renders the composition or dosage form non-liquid, such as solid or semi-solid.

As used herein, the term "lipophilic," refers to compounds that are not freely soluble in water; and the term "lipophilic surfactant" refers to surfactants that have HLB values of about 10 or less. Conversely, the term "hydrophilic" refers to compounds that are soluble in water; and term "hydrophilic surfactant" refers to surfactants that have HLB values of more than about 10.

As used herein, the term "ionizable fatty acid" refers to a fatty acid compound that changes its HLB as a function of pH. For example, oleic acid is predominantly lipophilic at lower pH values (such as those found in the stomach) but becomes a predominantly hydrophilic at higher pH values (such as those found in the intestine).

As used herein, "subject" refers to a mammal that may benefit from the administration of a drug composition or method of this invention. Examples of subjects include humans. In one aspect, the subject can be a human male. In another embodiment, the subject can be a hypogonadal male. In one aspect, the subject is a male in need of replacement therapy for conditions associated with a deficiency or absence of endogenous testosterone. As used herein, the testosterone deficiency or hypogonadism in a male human subject (hypogonadal male) refers to a condition wherein the average baseline plasma testosterone concentration (T-$C_{avg-B}$) is about 300 ng/dL or less. However, in some instances, testosterone deficiency or hypogonadism in a male human subject refers to a condition wherein the average baseline plasma testosterone concentration is about 400 ng/dL or less.

As used herein, "group" or "group of subjects" refers to a collection of at least 12 human male subjects who receive and respond to exogenous oral administration of the compositions disclosed herein, namely testosterone undecanoate-containing compositions. In one aspect, the group can include at least 100 or at least 300 male subjects. In another aspect, the group can include at least 1000 male subjects. In another embodiment, the subjects can be hypogonadal subjects.

The term "oral administration" represents any method of administration in which an active agent can be administered by swallowing, chewing, or sucking of the dosage form. The composition of the current inventions can be admixed with food or drink prior to being orally consumed.

As used herein, a "dosing regimen" or "regimen" such as an "initial dosing regimen" or a "maintenance dosing regimen" refers to how, when, how much, and for how long a dose of the compositions of the present invention can be administered to a subject. For example, an initial dosing regimen for a hypogonadal male subject may provide for a total daily dose of 450 mg administered in two divided doses at about 12 hours apart (e.g., once with breakfast and once with dinner) with meals (e.g., having about 10 g to 55 g of fat content, or any other appropriate meal) repeated daily for at least one week, two weeks or 30 days.

As used herein, "daily dose" refers to the amount of active agent (e.g., testosterone undecanoate) administered to a subject over a 24-hour period of time (e.g., per day). The daily dose can be administered as one or two or more administrations during the 24 hour period (twice-a-day). In one embodiment, the daily dose provides for two administrations in a 24 hour period. With this in mind, an "initial dose" or initial daily dose" refers to a dose administered during the initial regimen or period of a dosing regimen. An initial dose includes both the very first dose during the initial regimen as well as the subsequent doses during the same initial regimen. Similarly, a "maintenance dose" or "maintenance daily dose" refers to a dose administered during a maintenance regimen of a dosing regimen. It is worth noting that the maintenance dose follows a dose titration based on the serum testosterone determination on a titration node day (after a single dose of the initial daily dose at steady state), however the maintenance dose does not need to be of a different quantity as the initial dose or the previous maintenance dose (in the case of multiple titrations).

As used herein, the term "solidifying agent" or "solidifying additive" are used interchangeably and refer to a pharmaceutically acceptable additive that is in a solid physical state at 20° C. Similarly, a "solid lipophilic additive" refers to a lipophilic compound or component that is in a solid physical state at 20° C. and/or renders the composition or dosage form non-liquid, such as solid or semi-solid.

As used herein, "non-liquid" when used to refer to the state of a composition disclosed herein refers to the physical state of the composition as being a semi-solid or solid.

As used herein, "solid" and "semi-solid" refers to the physical state of a composition that supports its own weight at standard temperature and pressure, and has adequate viscosity or structure to not freely flow. Semi-solid materials may conform to the shape of a container under applied pressure.

As used herein, "titration" or "dose titration" or "dose adjustment" are used interchangeably and refer to an increase or decrease of the total daily dose of testosterone undecanoate administered to a subject, typically based on the response of the subject to the exogenous administered testosterone undecanoate. The dose can be increased or decreased based on the measurement of serum testosterone concentration after a steady state has been achieved.

As used herein, "steady state" refers to the achievement of a stable response in serum total testosterone levels to exogenously administered testosterone undecanoate, typically achieved after at least 15 days following the start of a dosing regimen.

As used herein, "initial daily dose" (IDD) or "Daily dose of the initial regimen" is a dose of testosterone undecanoate administered daily to a subject in need of testosterone therapy. The initial daily dose may be administered in one or two or more intervals over a 24-hour period, e.g., twice-a-day. Similarly, "maintenance daily dose" or "daily dose of the maintenance regimen" is a dose of testosterone undecanoate administered daily to a subject in need of testosterone therapy as determined based on measurement of the titration node day titration metric and is the daily dose going forward within a few days of measurement unless a dose change is needed based on a another titration node day measurement. During a maintenance regimen there may be one or two or more daily doses administered which at some point during the regime would be considered to be the maintenance daily dose.

As used herein, "titration node" or "titration node day" are used interchangeably and refer to a day on which a serum sample is drawn from a subject for measurement of the serum testosterone concentrations in order to determine whether a testosterone undecanoate dose titration is necessary and what the titration type might need to be. The measured serum testosterone levels may also be used to determine dose a titration metric to be utilized in deciding dose titration needs for an individual subject. As dosing regimens can include one or more titration node day the term may refer to a first titration node during a dosing regimen (e.g., between the initial dosing regimen and the maintenance dosing regimen) or it can refer to a subsequent titration node day between a maintenance dosing regimen and a subsequent maintenance dosing regimen.

As used herein, the terms "release" and "release rate" are used interchangeably to refer to the discharge or liberation of a substance, including without limitation a drug, from the dosage form into a surrounding environment such as an aqueous medium either in vitro or in vivo.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

The terms "plasma testosterone concentration," "testosterone concentration in the blood," and "serum testosterone concentration" are used interchangeably and refer to the "total" testosterone concentration which is the sum of the bioavailable testosterone including free and protein-bound testosterone concentrations. As with any bio-analytical measure, for increased consistency the method employed to measure initial serum testosterone levels should be consistent with the method used to monitor and re-measure serum testosterone levels during clinical testing and testosterone therapy for a subject. Likewise, serum or plasma (used interchangeably) testosterone undecanoate and the metabolites dihydrotestosterone and dihydrotestosterone undecanoate, can be determined by the ordinary skilled artisan.

As used herein, of the average serum testosterone concentration can be determined using methods and practices known in the art. For example, the average baseline plasma testosterone concentration of a human male is the arithmetic mean of the total plasma testosterone concentrations determined on at least two consecutive time points that are reasonably spaced from each other, for example from about 1 hour to about 168 hours apart. In a particular case, the plasma testosterone concentration can be determined on at least two consecutive times that are about 12 hours to about 48 hours apart. In another particular method, the plasma testosterone concentration of the human male can be determined at a time between about 5 am and about 11 am. Further, the plasma testosterone concentration can be the determined by standard analytical procedures and methods available in the art, such as for example, automated or manual immunoassay methods, liquid chromatography or liquid chromatography-tandem mass spectrometry (LC-MSMS) etc.

As used herein, the term $AUC_{0-t}$ is the area under the curve of a plasma-versus-time graph determined for the analyte from the time 0 to time "t".

As used herein, the term "$C_{avg}$," "$C_{ave}$," or "C-average" are used interchangeably, and is determined as the $AUC_{0-t}$ or the mean AUC divided by the time period (t). For example, $C_{avg-8\,h}$ is the average plasma concentration over a period of 8 hours post-dosing determined by dividing the $AUC_{0-8}$ value by 8. Similarly, $C_{avg-12\,h}$ is the average plasma concentration over a period of 12 hours post-dosing determined by dividing the $AUC_{0-12}$ value by 12; $C_{avg-24\,h}$ is the average plasma concentration over a period of 24 hours post-dosing determined by dividing the $AUC_{0-24\,h}$ value by 24, and so on. Unless otherwise stated, all $C_{ave}$ values are considered to be $C_{ave-24\,h}$.

As used herein "$C_{max}$" refers to the maximum measured serum concentration of the administered drug or a metabolite after single dose administration.

As used herein, "free of" or "substantially free of" of a particular compound or compositions refers to the absence of any separately added portion of the referenced compound or composition. Free of or substantially free of can include the presence of 1 wt % or less (based on total composition weight) of the referenced compound which may be present as a component or impurity of one or more of the ingredients.

As used herein, the term "TU" refers to testosterone undecanoate.

As used herein, "with a meal" generally means within an hour of a meal (e.g., plus/minus an hour or preferably within 30 minutes). More preferably, "with a meal" means within 30 minutes of a meal e.g., within 30 minutes after the subject has eaten a meal. Even more preferably, "with a meal" refers to about 30 minutes after the subject has eaten a meal.

As used herein, the terms "meal" and "food" can be used interchangeably.

As used herein, "low fat" or "low fat meal" generally refers a meal having less than about 30 grams of fat. For example, in some cases, "low fat" or "low fat meal" refers to a meal having from about 10 grams to about 30 grams of fat, or about 10 grams to about 25 grams of fat, or about 15 grams to about 25 grams of fat, or about 15 grams of fat.

As used herein, "medium fat," "medium fat meal," "standard fat," "standard meal," or "standard fat meal" generally refers to a meal having from about 20 grams of fat to about 50 grams of fat. For example, in some cases, "medium fat," "medium fat meal," "standard fat," "standard meal," or "standard fat meal" refer to a meal having from about 20 grams to about 45 grams of fat, about 20 grams to about 40 grams of fat, about 25 grams to about 35 grams of fat, or about 30 grams of fat.

As used herein, "high fat" or "high fat meal" generally refers to a meal having 40 or more grams of fat. For example, in some cases, "high fat" or "high fat meal" can refer to a meal having from about 40 to about 100 grams of fat, about 45 grams to about 100 grams of fat, about 45 grams to about 90 grams of fat, about 45 to about 75 grams of fat, about 45 grams to about 60 grams of fat, or about 50 grams. Further, in some other examples, "high fat meal" can be a meal having greater than 45 grams of fat or a meal having greater than 50 grams of fat.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Described herein are formulations and methods of using those formulations for testosterone replacement therapy. The formulations described herein are for oral administration for replacement therapy in a male for conditions associated with a deficiency or absence of endogenous testosterone (e.g., a hypogonadal male or a male experiencing a symptom of testosterone deficiency). In some aspects, the therapy can be used in females.

It is noted that testosterone deficiency can typically be associated with a variety of conditions, each of which can cause or contribute to the deficiency or absence of testosterone in a subject. The compositions and oral dosage capsules of the present invention can be used to treat any condition associated with testosterone deficiency, including complete absence, of endogenous testosterone. Examples of conditions associated with testosterone deficiency that can be treated using the oral dosage capsules and/or compositions of the present invention include, but are not limited to congenital or acquired primary hypogonadism, hypogonadotropic hypogonadism, cryptorchidism, bilateral torsion, orchitis, vanishing testis syndrome, orchidectomy, Klinefelter's syndrome, post castration, eunuchoidism, hypopituitarism, endocrine impotence, infertility due to spermatogenic disorders, impotence, male sexual dysfunction (MSD) including conditions such as premature ejaculation, erectile dysfunction, decreased libido, and the like, micropenis and constitutional delay, penile enlargement, appetite stimulation, testosterone deficiency associated with chemotherapy, testosterone deficiency associated with toxic damage from alcohol, heavy metal, or other substances, osteoporosis associated with androgen deficiency, late-onset hypogonadism (e.g., age-related), or combinations thereof.

Additionally, the compositions and oral dosage forms disclosed herein include can also be used to treat idiopathic gonadotropin, LHRH deficiency, or pituitary hypothalamic injury from tumors, trauma, or radiation. Typically, these subjects have low serum testosterone levels but have gonadotropins in the normal or low range. In one embodiment, the compositions or oral dosage forms can be used to stimulate puberty in carefully selected males with clearly delayed puberty not secondary to pathological disorder. In another embodiment, the compositions and oral dosage forms can be used in female-to-male transsexuals in order to maintain or restore male physical and sexual characteristics including body muscle mass, muscle tone, bone density, body mass index (BMI), enhanced energy, motivation and endurance, restoring psychosexual activity, etc. In some embodiments, the testosterone undecanoate compositions and oral dosage capsules can be useful in providing hormonal male contraception.

Additionally, testosterone therapy can also be used to improve the quality of life of subjects suffering from conditions such as decreased libido, diminishing memory, anemia due to marrow failure, renal failure, chronic respiratory or cardiac failure, steroid-dependent autoimmune disease, muscle wasting associated with various diseases such as AIDS, preventing attacks of hereditary angioedema or urticaria; andropause, and palliating terminal breast cancer. In some situations, certain biomarkers such as for example, increased SHBG levels, can be used to diagnose a subject who may be in need of testosterone therapy. These biomarkers can be associated with conditions/disease states such as anorexia nervosa, hyperthyroidism, hypogonadism, androgen insensitivity/deficiency, alcoholic hepatic cirrhosis, primary biliary cirrhosis, and the like."

In one specific embodiment, formulations and oral dosage forms as described herein can be used to treat primary hypogonadism (congenital or acquired) or hypogonadotropic hypogonadism (congenital or acquired).

The formulations can be any formulation having a testosterone ester e.g., testosterone undecanoate and one or more carriers. The carriers are selected such that the formulation, when administered orally for replacement therapy in a male for conditions associated with a deficiency or absence of endogenous testosterone, produces bioequivalent serum testosterone levels when administered with low, standard, or high fat meals. Bioequivalence can be determined by an ordinary skilled artisan in view of Examples described herein. The carriers and amounts thereof are selected such that the formulation provides bioequivalent levels of serum testosterone when administered under high fat meals versus low fat meals, standard meals versus low fat meals, standard meals versus high fat meals, or low, standard, or high fat meals.

In one embodiment, the composition or oral dosage form can be administered with a meal, such as a meal that provides about 200 calories to about 1000 calories of food energy. In another embodiment, the composition or oral dosage form can be administered with a meal that provides about 5%, 10%, 15%, 20%, 25%, 30%, 35%, 40%, 45%, 50%, 55%, 60%, 70%, 80%, 90% or 100% of the calories from the fat (or within a range derived from any combination of these values). In yet another embodiment, the composition or oral dosage form can be administered with a meal that provides about 5%, 10%, 15%, 20%, 25%, 30%, 35%, 40%, 45%, or 50% of the calories from the fat (or within a range derived from any combination of these values). In yet another embodiment, the composition of oral dosage form can be administered with a meal that provides about 10% to about 50% of the calories from the fat. In one aspect, where about 10% to about 50% of the calories are from the fat, the meal can include at least 10 grams or at least 15 grams of fat. In another embodiment, the composition or oral dosage form can be administered with a high-fat, high calorie meal. In another embodiment, the composition or oral dosage form can be administered with a standard meal that provides about 500 calories to about 1000 calories of energy. The compositional make-up of the meals that are administered can vary depending on the tastes and dietary needs of a subject. However, in some situations it may be beneficial to administer the compositions and oral dosage forms with meals that provide no fat to about 100 g of fat. In one embodiment, the meal can provide about 10 g to about 50 g of fat. In yet a further embodiment, the meal can provide 15 g to about 35 g of fat. In yet a further embodiment, the meal can provide about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 grams of fat (or within a range derived from any combination of these values).

It is noted that any type of food or meal can be used in the methods and with the compositions described herein depending on the particular embodiment or aspect of the invention. Typically, the amount of fat or calories per serving is available on the food label or otherwise provided, such as by a restaurant. Fat content or calories in food and meals can also be determined or estimated by an individual using the methods and compositions disclosed herein by consulting typical books on nutrition or nutritional databases such as those provided by the USDA (United States Department of Argiculture) which are available online.

Exemplary, breakfasts and foods with ≥15 g fat are given below, as provided by the USDA Nutrient Database (each of which can be modified to achieve a desired fat content, calorie content, or combination thereof, and are not intended to be limiting examples). The fat and calorie content of food or dinner meals can be similarly determined by consulting label information, online information and databases, nutrition books, information provided by restaurants, and the like.

1 cup toasted wheat germ cereal (12 g)+1 cup lowfat (2%) milk (5 g): 17 g fat 1 slice whole wheat toast (1 g)+2 Tablespoons peanut butter (16 g): 17 g fat 1 small bagel (1.5 g)+1.5 oz cream cheese (15 g): 16.5 g fat ½ cup homemade granola cereal (15 g): 15 g fat 2 boiled eggs (10 g)+1 oz turkey bacon (5 g): 15 g fat 2 boiled eggs (10 g)+1 slice whole wheat toast (1 g)+1 teaspoon butter (4 g): 15 g fat 1 medium butter croissant (12 g)+coffee with 1 Tablespoon cream (3 g): 15 g fat ¼ cup almonds, whole: 18 g fat ¼ cup sunflower seeds: 18 g fat 2 oz cheddar cheese: 18 g fat Other non-limiting examples of foods or meals that a subject can have with the compositions and methods disclosed herein can include, for example:

Mega Melt with Reg eggs, 6" sandwich, hash browns, 12 fl oz orange juice: 36 g fat (1014 kcal)

6" Subway Melt Omelet Sandwich with regular egg, hash browns, 12 fl oz orange juice: 37 g fat (1074 kcal)

6" sausage, eggs & cheese omelet sandwich, hash browns, 12 fl oz orange juice: 29 g fat (854 kcal)

Bacon, egg & cheese on 3" flatbread, hash brown, 12 fl oz orange juice: 28 g fat (814 kcal)

McDonalds hotcakes with sausage, syrup, hash browns: 33 g fat (850 kcal);

Fruit & maple oatmeal, hash browns, egg McMuffin, nonfat Latte: 34 g fat (980 kcal)

Panera cinnamon roll and strawberry granola parfait: 35 g fat (940 kcal)

Starbuck's bacon and gouda Artisan breakfast sandwich, steel cut oatmeal with blueberry topping, and greek yogurt with berries parfait: 31 g fat (920 kcal)

As will be recognized by one skilled in the art, there are numerous other food or meal options that can be used to arrive at a low, medium, or high fat meal.

Whether or not the compositions or oral dosage forms described herein are administered with a meal, the compositions and oral dosage forms can be used in a variety of regimens for testosterone replacement therapy and other treatments or therapies. For example, in one embodiment, a testosterone replacement therapy for twice daily oral dosing is provided comprising: (a) 2 (or 3) different dose strength oral dosage forms having different amounts of testosterone undecanoate; (b) 3 dosing regimens providing for 3 different daily doses of testosterone undecanoate; (c) both (a) and (b); or (d) a pharmaceutically equivalent version thereof. In one aspect, the testosterone replacement therapy provides steady state serum levels of testosterone ($C_{avg}$) to a male having testosterone deficiency or in need of said therapy in the range of about 300 ng/dL to about 1140 ng/dL. In one aspect, the testosterone replacement therapy provides steady state serum levels of testosterone ($C_{avg}$) to a male having testosterone deficiency or in need of said therapy in the range of about 400 ng/dL or 435 ng/dL to about 1140 ng/dL. In one aspect, the testosterone replacement therapy provides single dose $C_{max}$ levels of serum testosterone at steady state to a population of males (e.g., more than 30, 40, 50, 75, 100, 150 or 200 males) having testosterone deficiency, or in need of said therapy, of less than 2500 ng/dL in at least 95% of the population of males, less than 1500 ng/dL in at least 85% of the population of males; or a serum testosterone $C_{max}$ of about 1800 ng/dL to about 2500 ng/dL in 10% or less of the population of males having testosterone deficiency. In one aspect, the testosterone replacement therapy has one of the dosage forms having from about 140 to 160 mg testosterone undecanoate and the other dosage form has from about 215 mg to about 250 mg testosterone undecanoate. In one aspect, the testosterone replacement therapy can include a third dose strength that has from about 280 mg to about 320 mg of testosterone undecanoate. In one specific aspect, the third dose strength has about 300 mg testosterone undecanoate. In one aspect, the testosterone replacement therapy has one of the dosage forms having from about 145 to 155 mg testosterone undecanoate and the other dosage form has from about 220 mg to about 230 mg testosterone undecanoate. In one aspect, the testosterone replacement therapy has one the of dosage forms having about 150 mg testosterone undecanoate and the other dosage form has about 225 mg testosterone undecanoate. In one aspect, the testosterone replacement therapy has one the of dosage forms having from about 60 to 90 mg testosterone undecanoate and the other dosage form has from about 100 mg to about 130 mg testosterone undecanoate. In one aspect, the testosterone replacement therapy has one of the dosage forms having from about 70 to 80 mg testosterone undecanoate and the other dosage form has from about 107 mg to about 118 mg testosterone undecanoate. In one aspect, the testosterone replacement therapy has one of dosage forms having about 75 mg testosterone undecanoate and the other dosage form has about 112.5 mg testosterone. In one aspect, the testosterone replacement therapy has 3 dosing regimens providing for 3 different daily doses of testosterone undecanoate provide for a first daily dose of about 275 mg to about 325 mg of testosterone undecanoate, a second daily dose of from about 425 mg to about 490 mg of testosterone undecanoate and a third daily dose of about 575 mg to about 625 mg of testosterone undecanoate. In one aspect, the testosterone replacement therapy provides for 3 different daily doses of testosterone undecanoate—providing for a first daily dose of about 300 mg of testosterone undecanoate, a second daily dose of about 450 testosterone undecanoate and a third daily dose of about 600 mg of testosterone undecanoate. In one aspect, the testosterone replacement therapy comprises: 2 dosage forms, one having about 75 mg of testosterone undecanoate and the other dosage form having about 112.5 testosterone undecanoate; 3 dosing regimens, a first dosing regimen comprising administration of two dosage forms twice a day, each dosage form having about 75 mg testosterone undecanoate, a second dosing regimen comprising administration of two dosage forms twice a day each dosage form having about 112.5 mg testosterone undecanoate, and a third dosing regimen comprising administration of four dosage forms twice a day each dosage form having about 75 mg testosterone undecanoate or a pharmaceutically equivalent version thereof. In one aspect, the testosterone replacement therapy comprises: 2 dosage forms, one having about 150 mg of testosterone undecanoate and the other dosage form having about 225 testosterone undecanoate; 3 dosing regimens, a first dosing regimen comprising administration of one dosage form twice a day each dosage form having about 225 mg testosterone undecanoate, a second dosing regimen comprising administration of two dosage forms twice a day each dosage form having about 150 mg testosterone undecanoate, and a third dosing regimen comprising administration of two dosage forms twice a day each dosage form having about 150 mg testosterone undecanoate or a pharmaceutically equivalent version thereof. As described herein, administration refers to administration to a subject in need of testosterone replacement e.g., a hypogonadal male or a male having low testosterone levels or a symptom thereof. According to this embodiment, the dosage form can be a capsule with the fill containing at particular amount (e.g., 112.5 mg) of TU at about 15 wt % loading, 63 wt % Maisine 35-1, 16 wt % Cremophor RH 40, and 6 wt % PEG 8000 or a pharmaceutically equivalent formulation thereof, a bioequivalent formulation thereof, or a combination thereof. Thus, these results support a drug label that indicates or a method that includes that the oral testosterone replacement therapy (oral formulation) is taken (1) "WITH A MEAL" or (2) "WITH MEAL, BUT NOT ON EMPTY STOMACH" or (3) "WITH FAT CONTAINING FOOD" not specifying fat content. In an alternative aspect, the drug label may indicate or the method includes that the formulation is taken "WITH MEAL, BUT NOT LOW FAT". In an alternative aspect, the drug label may indicate or the method includes that the formulation is taken "WITH MEAL, BUT NOT HIGH FAT". In an alternative aspect, the drug label may indicate or the method includes that the formulation is taken "WITH STANDARD OR NORMAL MEAL".

Accordingly, an oral dosage form can be provided in a container having a label that indicates that the oral dosage is to be taken (1) "WITH A MEAL", (2) "WITH MEAL, BUT NOT ON EMPTY STOMACH", (3) "WITH FAT CONTAINING FOOD" not specifying fat content, (4) "WITH MEAL, BUT NOT LOW FAT", (5) "WITH MEAL, BUT NOT HIGH FAT", or (6) "WITH STANDARD OR NORMAL MEAL". Other suitable labels can also be included on the label of the container, such as those described herein. Any suitable container can be used. Non-limiting examples of suitable containers can include a bottle, a pouch, a blister package, and other similar packaging that is known in the art.

As described herein an oral TRT (testosterone replacement therapy) is provided. The TRT has three different daily doses which commence with an initial dosing regimen having a specific daily dose of testosterone undecanoate that lasts for a period of time e.g., at least 1, 2, 3, 4, 5, 6, 7, 8, 9, 10, 11, 12, 13, 14, 15, or 16 weeks. After this period of time on the initial dosing regimen, a dose titration measurement or assessment is made. The purpose of the dose titration assessment or measurement is to determine if the daily dose should remain the same as a daily dose of the initial regimen or whether the daily dose should be increased or decreased. The dose titration measurement or assessment is made by determining serum testosterone concentrations within a specific amount of time (e.g., window of time) after administration of a single dose of the initial regimen at steady state. Three options are possible based on the result of this measurement or assessment. A level of serum testosterone that is too high will result in a decrease in the total daily dose of testosterone undecanoate, a level of serum testosterone that is too low will result in an increase in the daily dose of testosterone undecanoate and intermediate levels of serum testosterone will result in no change of the daily dose of testosterone undecanoate. It was surprisingly found that the TRT described herein provides numerous benefits to individuals or populations of individuals in need of such therapy and in particular it was found that certain formulations are bioequivalent with respect to different food conditions. Thus, the oral dosage forms used in the TRT can be (1) "WITH A MEAL" or (2) "WITH MEAL, BUT NOT ON EMPTY STOMACH" or (3) "WITH FAT CONTAINING FOOD" not specifying fat content. In an alternative aspect, the drug label may indicate or the method includes that the formulation is taken "WITH MEAL, BUT NOT LOW FAT". In an alternative aspect, the drug label may indicate or the method includes that the formulation is taken "WITH MEAL, BUT NOT HIGH FAT". In an alternative aspect, the drug label may indicate or the method includes that the formulation is taken "WITH STANDARD OR NORMAL MEAL". The TRT described herein provides for three different daily doses of testosterone undecanoate formulated for oral administration that are typically divided into two administrations e.g., a morning dose and an evening dose. The three daily doses of testosterone undecanoate are in the 280-320 mg range, the 430 mg to 490 mg range, and the 580 mg to 620 mg range. These daily doses are provided by two to eight unit dosage forms per day.

According to this TRT, a subject or patient e.g., hypogonadal male starts on an initial dose or initial dosing regimen that provides a specific amount of testosterone undecanoate per day for an initial period of time (e.g., greater than one, two, or three weeks) that is to be administered with food. This initial daily dose is in the range of about 430 mg to 490 mg TU per day (or 435 mg to 465 mg TU per day, 440 mg to 460 mg TU per day, 445 mg to 455 mg TU per day, or about 450 mg per day). After the initial period of time, a dose titration measurement or assessment is made. The dose titration measurement is made by determining serum testosterone levels at a specific time (e.g., within 1 to 12 hours, 1 to 11 hours, 1 to 10 hours, 1 to 9 hours, 1 to 8 hours, 1 to 7 hours, 1 to 6 hours, 1 to 5 hours, 1 to 4 hours, 2 to 10 hours, 2 to 9 hours, 2 to 8 hours, 2 to 7 hours, 2 to 6 hours, 2 to 5 hours, 2 to 4 hours, 1 to 3 hours, 2 to 3 hours, 3 to 4 hours, 4 to 5 hours, 3 to 5 hours, 4 to 6 hours, 3 to 6 hours, 3 to 8 hours, or 4 to 6 hours; or at about 1, 2, 3, 4, 5, 6, 7, 8, 9, 10, 11, or 12 hours±0.5, 1, 1.5, or 2 hours) after a single dose of the initial regimen when the patient is at steady state. Depending of the serum testosterone level obtained from the dose titration measurement, the patient can receive a maintenance regimen that has the same daily dose as the initial regimen or the daily dose is increased or decreased. Typically, the patient or subject is then maintained on the maintenance regimen, although one or more additional dose titration measurements or dose titrations can be made. The therapy described herein is typically administered as a twice a day therapy with a meal, so a 300 mg TU dose is administered as 150 mg with a meal twice a day; a 450 mg dose is administered as 225 mg with a meal twice a day; and a 450 mg dose is administered as 225 mg with a meal twice a day.

The dose titration of the TRT described herein was found to be surprisingly robust and beneficial for patients receiving the therapy, especially in view of the food effect study described in the Examples. In a specific aspect, the up or down titration are at about 70 to 80 mg TU per dose (e.g., 75 mg TU) or about 140 to 160 mg (e.g., 150 mg TU) per day TU. Typically, the doses of TU are administered with a meal. Thus, the methods described herein can include an initial daily dose followed by a dose titration. The dose titration is used to determine the maintenance daily dose which is within plus/minus 75%, 50%, 40% or 35% of the initial daily dose.

In one embodiment, a therapy for treating a male having a baseline serum testosterone level of 300 ng/dL or less is provided, said therapy comprising: (a) 2 oral dosage forms having different amounts of testosterone undecanoate; (b) 3 dosing regimens providing different daily doses of testosterone undecanoate; (c) both (a) and (b); or (d) a pharmaceutically equivalent version thereof. In one aspect, the higher and lower daily doses are within about 40% of the intermediate dose. In one aspect, the therapy provides single dose $C_{max}$ levels of serum testosterone at steady state levels to a population of males having testosterone deficiency, or in need of said therapy, of (a) less than 2500 ng/dL in at least 95% of the population of males; (b) less than 1500 ng/dL in at least 85% of the population of males; a serum testosterone $C_{max}$ of about 1800 ng/dL to about 2500 ng/dL in 10% or less of the subjects in the group; or a combination thereof. In one aspect, a patient receiving the therapy has a dose titration assessment. In one aspect, the dose titration assessment comprises determining a value of serum testosterone at from about two to eight hours after receiving a dose of testosterone undecanoate. In one aspect, a patient having (a) a low serum testosterone level at two to eight hours after receiving a single dose of testosterone undecanoate at steady state receives a higher dose of testosterone undecanoate; (b) a high serum testosterone level at two to eight hours after receiving a single dose of testosterone undecanoate at steady state receives a lower dose of testosterone undecanoate; (c) an intermediate serum testosterone level after receiving a single dose of testosterone undecanoate at steady state an intermediate dose of testosterone undecanoate; or (d) a combination thereof. In one aspect, the dose titration assessment comprises determining the serum testosterone level during a window period within two to eight hours after receiving a dose of testosterone undecanoate. Low serum testosterone can be defined as less than 500, 450, 400, 350, 300, 250 or 200 ng/dL. High serum testosterone can be defined as greater than 500, 550, 600, 650, 700, 750, 800 or 850 ng/dL. Intermediate serum testosterone can be defined as a range of values defined by low and high serum testosterone levels in the previous two sentences.

Typically, the unit dosage forms contain an amount of TU as described herein and one or more pharmaceutically acceptable carriers e.g., additives. In one aspect, the unit dosage form is a tablet or capsule. In one aspect, the unit dosage form has a pharmaceutically acceptable carrier lipophilic additive, a hydrophilic additive, a solidifying agent or a combination thereof. In one aspect, the unit dosage form when tested using a USP type 2 apparatus in about 1000 mL 8% w/v Triton X100 solution in water at 37.0±0.5 at 100 rpm releases at least 60 wt % TU at 15 minutes and less than 100 wt % TU at 15 minutes. In one aspect, the unit dosage form has a pharmaceutically acceptable carrier lipophilic additive, a hydrophilic additive, a solidifying agent, or a combination thereof. In one aspect, the unit dosage form when tested using a USP type 2 apparatus in about 1000 mL 8% w/v Triton X100 solution in water at 37.0±0.5 at 100 rpm releases less than 90 wt % TU at 30 minutes and greater than 90 wt % TU at 120 minutes. In one aspect, the unit dosage form when tested using a USP type 2 apparatus in about 1000 mL 8% w/v Triton X100 solution in water at 37.0±0.5 at 100 rpm releases greater than 90 wt % TU at 30 minutes. The unit dosage forms usually contain a lipophilic additive although this is not absolutely required. The dosage forms can also contain a hydrophilic additive, a solidifying agent, or one or more other additives. The pharmaceutically acceptable carriers a selected such that the oral dosage form is pharmaceutically equivalent, bioequivalent, in respect to serum testosterone levels to a capsule with the fill containing from 50 mg to 350 mg TU (e.g., 75 or 112.5 mg TU) at about 15 wt % loading, 63 wt % Maisine 35-1, 16 wt % Cremophor RH 40, and 6 wt % PEG 8000). In respect to bioequivalent formulations, in one aspect, bioequivalent refers to steady state. In another aspect, bioequivalent refers to single dose. In yet another aspect, bioequivalent refers to food effect bioequivalent. Food effect bioequivalent refers to bioequivalence of the formulation under low fat versus standard fat meals, standard fat versus high fat meals, low fat versus high fat meals or a combination thereof.

In one embodiment, specific examples of oral dosage forms that are bioequivalent, pharmaceutically equivalent or both, to a capsule with the fill containing from 50 mg to 350 mg TU (e.g., 75 or 112.5 mg TU) at about 15 wt % loading, 63 wt % Maisine 35-1, 16 wt % Cremophor RH 40, and 6 wt % PEG 8000) include tablets, capsules, sachets, lozenges, granules, powders, sprinkle, suspension, liquids or combinations thereof. In another embodiment, the dosage form is coated. In one embodiment, the solid composition can be a matrix. In one embodiment, the solid oral dosage form is a tablet or a capsule. In another embodiment oral dosage form is a multiparticulate oral dosage form. In another embodiment, the composition can be multiparticulate. Regardless of the type, the oral dosage forms or compositions can be formulated to provide immediate, modified, delayed, sustained, extended, and/or controlled release of the testosterone undecanoate. The immediate, modified, delayed, extended, pulsatile, and/or controlled release can be achieved by any method known in the art so long as it does not interfere with the function of the solid oral dosage forms. Non-limiting examples of such methods includes coatings, polymers, and the like. In one embodiment, the oral dosage form can be uncoated. In one embodiment the solid composition of the invention is a solid dispersion, solid solution, molecular dispersion, co-precipitate, amorphate, solidified suspension, admixture, eutectic mixture, melt extrude, drug-carrier complex, thermosetting system, or combinations thereof. Thus, the oral dosage form has a drug label indicating or the method includes that the oral testosterone replacement therapy (oral formulation) is taken (1) "WITH A MEAL" or (2) "WITH MEAL, BUT NOT ON EMPTY STOMACH" or (3) "WITH FAT CONTAINING FOOD" not specifying fat content. In an alternative aspect, the drug label may indicate or the method includes that the formulation is taken "WITH MEAL, BUT NOT LOW FAT". In an alternative aspect, the drug label may indicate or the method includes that the formulation is taken "WITH MEAL, BUT NOT HIGH FAT". In an alternative aspect, the drug label may indicate or the method includes that the formulation is taken "WITH STANDARD OR NORMAL MEAL".

In some embodiments, the oral dosage forms the present invention can be manufactured as tablet or capsule dosage forms either by dry granulation methods, or by wet granulation methods. For example, testosterone undecanoate can be combined with one or more pharmaceutically acceptable carrier and blended to get a homogenous mixture which can be compressed into a tablet or disposed into a capsule. In another embodiment, the homogenous mixture can be kneaded with a binder solution to get a wet granulate mass which can be dried and sized, for example by passing through ASTM mesh #30. The resulting granules can be optionally blended with pharmaceutical aids such as diluents, lubricants, disintegrants etc., and disposed into capsules or compressed into tablets. In another particular case, the tablets can be coated. In one embodiment the tablet is a matrix tablet. In another embodiment, the tablet can be multi-layered tablet dosage form which can achieve release characteristics that can accommodate dose splitting.

The oral dosage forms can also be formulated using melt-extrusion processes alone or in combination with other known processes. For example, in one embodiment, an amount of testosterone undecanoate can be homogeneously combined with a sufficient amount of one or more carrier substances prior to undergoing extrusion. The carrier suitable for the compositions of this invention, specifically melt extrusion process, can be lipophilic or hydrophilic carrier. Combinations of lipophilic and hydrophilic carriers may also be used.

The terms "melt" and "melting" should be interpreted broadly, and include not only the alteration from a solid state to a liquid state, but can also refer to a transition to a glassy state or a rubbery state in which it is possible for one component of the mixture to get embedded more or less homogeneously into the other. In particular cases, one component can melt and the other component(s) can dissolve in the melt, thus forming a solution which, upon cooling, may form a solid composition having advantageous properties. In another particular case, one component can melt and the other component(s) can suspend thus forming a suspension which upon cooling may form a solid suspension having advantageous properties.

The melt-extruded solid compositions used to make the oral dosage forms of the present disclosure can be granular, multiparticulates, pellets, beads, mini-tablets or tablets. The melt-extruded solids can be used alone as the solid oral dosage form or can be disposed into capsules or formed into tablets.

The carrier for a melt-extruded composition and/or dosage form can include, but is not limited to, carriers such as ethyl cellulose, cellulose acetate phthalates, glyceryl distearate, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly (methacrylic acid) (anhydride), methyl methacrylate, polymethacrylate, stearic acid, poly(methyl methacrylate) copolymer, polyacrylamide, aminoalkyl methacrylate copolymer, poly(methacrylic acid anhydride), and glycidyl methacrylate copolymers.

In one embodiment, the carrier for a melt-extruded oral dosage form can be one or more pharmaceutically acceptable polymers including, but not limited to polyvinyl alcohol, polyvinyl pyrrolidone, polyethylene glycols having molecular weight of about 1000 to about 20,000, gelatin, carbomer, poloxamer, hydroxypropyl methyl cellulose; hydroxypropyl ethyl cellulose hydroxypropyl cellulose, and carboxymethyl cellulose. It is noteworthy that some pharmaceutical carriers can be used in more than one manufacturing process, such as a wet milling or dry milling process as well as a melt extrusion process.

In certain embodiments, the at least one pharmaceutically acceptable carrier of any pharmaceutical composition provided herein comprises at least one hydrophilic carrier. In specific embodiments, the hydrophilic carrier is a hydrophilic triglyceride. In more specific embodiments, the hydrophilic triglyceride is a polyoxylated castor oil, or a polyoxylated hydrogenated castor oil. In some embodiments, any pharmaceutical composition provided herein has a lipophilic carrier (e.g., additive) or combination of lipophilic carriers. In certain embodiments, any pharmaceutical composition provided herein comprises a lipophilic carrier and less than 10 wt % or less than 5 wt % of a hydrophilic carrier.

In one embodiment, the lipophilic additive can include a lipophilic surfactant.

As used herein a surfactant is considered to be a lipophilic surfactant when it has an HLB value of 10 or less. Various lipophilic surfactants can be used including, but not limited to mono-, di-glycerides of fatty acids like glyceryl monolinoleate (e.g., Maisine® 35-1), mono- and di glycerides of caprylic, capric acid (e.g., Capmul® MCM), glyceryl monooleate, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g., Labrafil® M 2125 CS), PEG-6 almond oil (e.g., Labrafil®M 1966 CS), PEG-6 apricot kernel oil (e.g., Labrafil®M 1944 CS), PEG-6 olive oil (e.g., Labrafil®M 1980 CS), PEG-6 peanut oil (e.g., Labrafil®M 1969 CS), PEG-6 hydrogenated palm kernel oil (e.g., Labrafil®. M 2130 BS), PEG-6 palm kernel oil (e.g., Labrafil® M 2130 CS), PEG-6 triolein (e.g., Labrafil® M 2735 CS), PEG-8 corn oil (e.g., Labrafil® WL 2609 BS), PEG-20 corn glycerides (e.g., Crovol® M40), PEG-20 almond glycerides (e.g., Crovol® A40), lipophilic polyoxyethylene-polyoxypropylene block co-polymers (e.g., Pluronic® L92, L101, L121 etc.); propylene glycol fatty acid esters, such as propylene glycol monolaurate (e.g., Lauroglycol FCC), propylene glycol ricinoleate (e.g., Propymuls), propylene glycol monooleate (e.g., Myverol P-O6), propylene glycol dicaprylate/dicaprate (e.g., Captex® 200), and propylene glycol dioctanoate (e.g., Captex® 800), propylene glycol mono-caprylate (e.g., Capryol® 90); propylene glycol oleate (e.g., Lutrol OP2000); propylene glycol myristate; propylene glycol mono stearate; propylene glycol hydroxy stearate; propylene glycol ricinoleate ; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g., Arlacel® 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g., Arlacel 20), sorbitan monopalmitate (e.g., Span-40), sorbitan monooleate (e.g., Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, and the like, and mixtures thereof. It is important to note that some lipophilic surfactants may also function as the solubilizer component of the compositions and oral dosage forms.

In one embodiment, the lipophilic surfactant can be selected from the group consisting of glyceryl monolinoleate (e.g., Maisine® 35-1), mono- and di glycerides of caprylic, capric acid (e.g., Capmul® MCM), glyceryl monooleate, propylene glycol mono caprylate, propylene glycol oleate, propylene glycol monostearate, propylene glycol monolaurate, propylene glycol mono-oleate, propylene glycol dicaprylate/dicaprate, sorbitan monooleate, PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, sorbitan monolaurate (e.g., Arlacel 20), sorbitan monopalmitate, sorbitan monooleate, sorbitan monostearate, sorbitan tristearate, sorbitan monolaurate, sorbitan monopalmitate, sorbitan monooleate, sorbitan trioleate, sorbitan sesquioleate, sorbitan tristearate, sorbitan monoisostearate, and combinations thereof. In some embodiments, the lipophilic surfactants can comprise at least about 10, 20, 30, 40, 50, 60, 70, 80, or 90 wt % of the total pharmaceutically acceptable carrier. It should be noted that the combinations of two or more lipophilic surfactants from the same or different classes therein are also within the scope of this invention and are together can be referred to as the lipophilic surfactant, unless otherwise stated.

In one embodiment, the composition/dosage form has a hydrophilic additive or a hydrophilic additive which can be a hydrophilic surfactant. A surfactant is considered to be a hydrophilic surfactant when it has an HLB value of greater than 10. Non-limiting examples of hydrophilic surfactants include non-ionic surfactants, ionic surfactants and zwitterionic surfactants. Specifically the hydrophilic surfactants suitable for the current invention include, but not limited to alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol and the like It should be noted that the combinations of two or more hydrophilic surfactants from the same or different classes are within the scope of this invention and are together can be referred to as the hydrophilic surfactant unless explicitly specified. In one embodiment, the hydrophilic additive can be a hydrophilic surfactant. Non-limiting examples of hydrophilic surfactants can include PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, and mixtures thereof.

Suitable additives utilized in various embodiments described herein include, by way of non-limiting example, adsorbing agents, anti-adherents, anticoagulants, antifoaming agents, antioxidants, anti-caking agents, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent, solvents, solubilizers, spreading agent sweeteners, stabilizers, surface area enhancing agents, suspending agent, thickeners, viscosity increasing agents, waxes and mixtures thereof.

Some non-limiting examples of the additives suitable for the present disclosure may be: alcohols and/or polyols (e.g., ethanol, isopropanol, butanol, benzyl alcohol, ethylene glycol, propylene glycol, glycerol, sorbitol, mannitol, dimethyl isosorbide, polyethylene glycol, fatty acid alcohol, vinyl alcohol polypropylene glycol, polyvinylalcohol, tocopherols, cellulose cyclodextrins, other derivatives, forms, mixtures thereof, or the like); ethers of polyethylene glycols having an average molecular weight of about 200 to about 20,000 (e.g., tetrahydrofurfuryl alcohol PEG ether, methoxy PEG, or the like); amides (e.g., 2-pyrrolidone, 2-piperidone, 8-caprolactam, N-alkylpyrrolidone, N-hydroxyalkylpyrrolidone, N-alkylpiperidone, N-alkylcaprolactam, dimethylacetamide, polyvinylpyrrolidone and the like.); esters (e.g. ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, δ-caprolactone and isomers thereof, ε-valerolactone and isomers thereof, gamma-butyrolactone and isomers thereof; and other additives known in the art, such as dimethyl acetamide, dimethyl isosorbide, N-methylpyrrolidones, monooctanoin, diethylene glycol monoethyl ether, or the like); amino acids (e.g., p-aminobenzamidine, sodium glycocholate) mesylate; amino acids and modified amino acids (e.g., aminoboronic acid derivatives and n-acetylcysteine; peptides and modified peptides (e.g., bacitracin, phosphinic acid dipeptide derivatives, pepstatin, antipain, leupeptin, chymostatin, elastin, bestatin, phoshporamindon, puromycin, cytochalasin potatocarboxy peptidase inhibitor, amastatin, or the like); polypeptide protease inhibitors; mucoadhesive polymers (e.g., polyacrylate derivatives, chitosan, cellulosics, chitosan-EDTA, chitosan-EDTA-antipain, polyacrylic acid, carboxymethyl cellulose etc.) or the like; or combinations thereof.

Some more examples of suitable additives for compositions and/or dosage forms described herein include, by way of non-limiting example, talc, magnesium stearate, silica (e.g., fumed silica, micronized silica, magnesium aluminum silicate etc.) and/or derivatives, polyethylene glycols, surfactants, waxes, oils, cetyl alcohol, polyvinyl alcohol, stearic acid, stearic acid salts, stearic acid derivatives, starch, hydrogenated vegetable oils, hydrogenated castor oils, sodium benzoate, sodium acetate, leucine, PEG, alkyl sulfate salts; acetylated monoglycerides; long-chain alcohols; silicone derivatives; butylated hydroxy toluene (BHT), butylated hydroxyl anisole (BHA), gallic acid, propyl gallate, ascorbic acid, ascorbyl palmitate, 4-hydroxymethyl-2,6-di-tert-butyl phenol, dry starch, dry sugars, polyvinyl pyrrolidones, starch paste, methacrylic copolymers, bentonite, sucrose, polymeric cellulose derivatives, shellac, sugar syrup; corn syrup; polysaccharides, acacia, tragacanth, guar gum, xanthan gums; alginates; gelatin; gelatin hydrolysate; agar; sucrose; dextrose; PEG, vinyl pyrrolidone copolymers, poloxamers; pregelatinized starch, sorbitol, glucose); acetic acid, hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, vinegar, pharmaceutically acceptable bases, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamin; salt of a pharmaceutically acceptable cation and an anion; EDTA and EDTA salts; titanium dioxide, food dyes, lakes, natural vegetable colorants, iron oxides, silicates, sulfates, magnesium hydroxide and aluminum hydroxide; halogenated hydrocarbons, trichloroethane, trichloroethylene, dichloromethane, fluorotrichloromethane, diethylether, trehalose, phosphates, citric acid, tartaric acid, gelatin, dextran and mannitol, lactose, mannitol, sodium chloride, potassium chloride, spray-dried lactose, hydrolyzed starches, directly compressible starch, microcrystalline cellulose, cellulosic derivatives, sorbitol, sucrose, sucrose-based materials, calcium sulfate, dibasic calcium phosphate, dextrose, croscarmellose sodium, starch, starch derivatives, clays, gums, cellulose, cellulose derivatives, alginates, crosslinked polyvinylpyrrolidone, sodium starch glycolate and microcrystalline cellulose, magnesium oxide, magnesium carbonates; desensitizers, spray-dried flavors, essential oils, ethyl vanillin, styrene/divinyl benzene copolymers, quaternary ammonium compounds, polyethylene glycol, citrate esters (such as triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl sebacate, ascorbic acid, boric acid, sorbic acid, benzoic acid, and salts thereof, parabens, phenols, benzyl alcohol, and quaternary ammonium compounds; alcohols, ketones, esters, chlorinated hydrocarbons water; sweeteners (e.g., maltose, sucrose, glucose, sorbitol, glycerin and dextrins, aspartame, saccharine, saccharine salts, glycyrrhizin), viscosity modifiers, sugars, polyvinylpyrrolidone, cellulosics, polymers, gums and/or alginates.

In one embodiment, additives may also be materials such as proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum Arabic); spermaceti; natural or synthetic waxes; carnuaba wax; fatty acids (e.g., stearic acid, hydroxystearic acid); fatty alcohols; sugars; shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based polymers (e.g., ethyl cellulose, methyl cellulose, microcrystalline cellulose, sodium carboxymethyl cellulose, hydroxypropylmethyl cellulose, ethyl cellulose, hydroxypropyl cellulose, HPMC acid succinates, cellulose acetate, cellulose nitrate, cellulose acetate butyrate, cellulose acetate trimellitate, carboxymethylethyl cellulose, hydroxypropylmethyl cellulose phthalate), shellacs; inorganics, such as dicalcium phosphate, hydroxyapatite, tricalcium phosphate, talc and titania; polyols, such as mannitol, xylitol and sorbitol; polyethylene glycol esters; and polymers, such as alginates, poly(lactide coglycolide), gelatin, crosslinked gelatin, and agar-agar. Non-limiting examples of compounds (e.g., additives) that can be used as at least a part of the pharmaceutically acceptable carrier include without limitation celluloses; dextrins, gums, carbomers, methacrylates, sugars, lactoses, inorganic carbonates, oxides, chlorides, sulphates and the like; salts of calcium; salts of magnesium; salts of fatty acids; inorganic and organic acids, bases and salts; propylene glycol; glycerols; fatty acids; fatty alcohols; fatty acid esters; glycerol esters; mono-, di- or triglycerides; edible oils; omega oils; vegetable oils, hydrogenated vegetable oils; partially or fully hydrogenated vegetable oils; glycerol esters of fatty acids; waxes; alcohols; gelatin; polyethylene glycol; polyethylene oxide co-polymers; silicates; antioxidants, tocopherols, sugar stearates, starches, shellac, resins, proteins, acrylates; methyl copolymers; polyvinyl alcohol; starch; phthalates; and combinations thereof.

In one embodiment, the additive may include at least one component selected from celluloses, dextrins, gums, carbomers, methacrylates, inorganic carbonates, salts of calcium, salts of magnesium, fatty acids, fatty acid esters, gelatin, lactoses, polyethylene glycol, polyethylene oxide co-polymers, silicates, partially hydrogenated vegetable oils, fully hydrogenated vegetable oils, waxes, antioxidants, tocopherol, sugar stearates, starches, shellac, resins, proteins, and combinations thereof.

In another embodiment, the additive may include at least one component selected from celluloses, dextrins, gums, carbomers, methacrylates, sugars, lactoses, inorganic carbonates, salts of calcium, salts of magnesium, salts of fatty acids, inorganic and organic acids, bases and salts, propylene glycol, glycerols, fatty acids, fatty alcohols, fatty acid esters, glycerol esters, mono-glycerol esters of fatty acids, di-glycerol esters of fatty acids, mixtures of mono-glycerol and di-gylcerol esters of fatty acids, omega oils, waxes, alcohols, gelatin, polyethylene glycol, polyethylene oxide co-polymers, silicates, antioxidants, tocopherol, sugar stearates, starches, shellac, resins, proteins, acrylates, methyl copolymers, polyvinyl alcohol, starch, phthalates, and combinations thereof.

Non-limiting examples of additives as release modulators that may be used include lipophilic resins; ethyl cellulose (EC), methylethyl cellulose (MEC), carboxymethyl ethylcellulose (CMEC), hydroxyethyl cellulose (HEC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropyl methyl cellulose phthalate (HPMCP), hydroxypropyl methyl cellulose acetate succinate (HPMCAS), hydroxypropyl methyl cellulose acetate trimellitate (HPMCAT), ion-exchange resin; poloxamers; and ethylhydroxy ethylcellulose (EHEC) tocopherol; shellac; and combinations thereof. Non-limiting examples of lipidic lipophilic release modulators include fatty acids; mono-, di-, tri-esters of fatty acids with glycerol; sucrose esters with fatty acids; cetyl alcohol; stearic acid; glyceryl monostearate; glyceryl distearate; glyceryl tristearate; glyceryl palmitostearate; hydrogenated castor oil; butyl and glycol esters of fatty acids; oleic acid; cetyl alcohol; stearyl alcohol; cetostearyl alcohol; hydrogenated vegetable oil; waxes; bees wax; lard; omega fatty acid esters; hydrogenated soybean oil; hydrogenated vegetable oil; hydrogenated cottonseed and castor oil; partially hydrogenated soybean oil; partially hydrogenated castor oil; partially soy and cottonseed oil; phospholipids; hydrogenated oils, and their derivatives and combinations thereof.

In some embodiments, the pharmaceutical composition (e.g., oral dosage form) provided herein is formulated, e.g., with a viscosity enhancing agent or solidifying agent, to provide a solid, a semi-solid, a gel, a jelly, a paste, or the like. In some embodiments, the oral dosage form is a liquid. Non-limiting examples of formulations (and for use in the methods described herein) are given in the tables below.

TABLE A

| Component | Capsule A1 % w/w | Capsule A2 % w/w |
|---|---|---|
| Testosterone Undecanoate (50-350 mg) | 1-50 | 10-30 |
| Hydrophilic Carrier | 0-90 | 0-30 |
| Lipophilic Carrier | 1-90 | 40-70 |
| Other Additive(s) | 0-20 | 0-10 |

TABLE B

| Component | Capsule B1 % w/w | Capsule B2 % w/w |
|---|---|---|
| Testosterone Undecanoate (75, 112.5, 150, 225, or 300 mg) | 1-50 | 10-30 |

TABLE B-continued

| Component | Capsule B1 % w/w | Capsule B2 % w/w |
|---|---|---|
| Hydrophilic Carrier | 0-90 | 0-30 |
| Lipophilic Carrier | 1-90 | 40-70 |
| Other Additive(s) | 0-20 | 0-10 |

TABLE C

| Component | Capsule C1 % w/w | Capsule C2 % w/w |
|---|---|---|
| Testosterone Undecanoate (75, 112.5, 150, 225, or 300 mg) | 5-40 | 10-30 |
| Hydrophilic Carrier | 0-90 | 0-30 |
| Lipophilic Carrier | 1-90 | 40-70 |
| Solidifying Agent | 1-20 | 3-10 |

TABLE D

| Component | Capsule D1 % w/w | Capsule D2 % w/w |
|---|---|---|
| Testosterone Undecanoate (75, 112.5, 150, 225, or 300 mg) | 5-40 | 10-30 |
| Cremophor RH 40 | 0-90 | 0-30 |
| Glyceryl Monolinoleate | 1-90 | 40-70 |
| PEG 8000 | 1-20 | 3-10 |

TABLE E

| Component | Capsule E1 % w/w | Capsule E2 % w/w |
|---|---|---|
| Testosterone Undecanoate (75, 112.5, 150, 225, or 300 mg) | 10-25 | 13-23 |
| Cremophor RH 40 | 0-25 | 10-20 |
| Glyceryl Monolinoleate | 30-90 | 40-70 |
| Solidifying agent | 0-20 | 3-10 |

Bioequivalent, pharmaceutically equivalent formulations having the drug label as described herein or for use in the method included herein can include those described about in Tables A-E or e.g., in reference to a formulation having 50 mg to 350 mg testosterone undecanoate (e.g., in one aspect either 75 mg or 112.5 mg TU) at about 15 wt % loading, about 63 wt % Maisine 35-1, about 16 wt % Cremophor RH 40, and about 6 wt % PEG 8000 as follows.

(1) Varying the loading (or amount) of testosterone undecanoate.

(2) Varying the amount of Maisine 35-1, exchanging Maisine 35-1 for another lipophilic additive (in varying amounts) or including one or more additional lipophilic additives in addition to Maisine 35-1 (in varying amounts). In one aspect, the other lipophilic additive is a fatty acid or ester thereof such as a fatty acid glyceride (e.g., mono-, di- or tri-glyceride) or a reaction mixture of a fatty acid glyceride with an alcohol e.g., polyethylene glycol, or a combination thereof.

(3) Varying the amount of Cremophor RH 40, exchanging Cremophor RH 40 for another hydrophilic additive (in varying amounts) or including one or more additional hydrophilic additives in addition to Cremophor RH 40 (in varying amounts). In one aspect, the other hydrophilic additive is a polyoxylated hydrogenated vegetable oil. In another aspect, the other hydrophilic additive is an ionic or non-ionic surfactant.

(4) Varying the amount of PEG 8000 (or not include PEG 8000), exchanging PEG 8000 for another solidifying agent (in varying amounts) or including one or more additional solidifying agents in addition to PEG 8000 (in varying amounts). In one aspect, the other solidifying agent is a high molecular weight PEG (2000 mw or more), a phytosterol or ester thereof, solid (at room temperature) fatty acids or mono- or di-glycerides) and the such.
(5) Including one or more additional pharmaceutically acceptable carriers (in varying amounts); or
(6) A combination of one or more of (1)-(5).

EXAMPLES

The following examples are provided to promote a more clear understanding of certain embodiments of the present invention, and are in no way meant as a limitation thereon.

Example 1

Food Effect Clinical Study

This study was a single-center, open-label, randomized, cross-over, single-dose, four period, four-treatment study to examine the effect of food (fasted vs. high fat) and fat content of food on pharmacokinetics of testosterone & metabolites. 14 subjects were enrolled and 13 completed the study. 225 mg of TU (2 capsules (capsule fill containing 112.5 mg TU at about 15 wt % loading, 63 wt % Maisine 35-1, 16 wt % Cremophor RH 40, and 6 wt % PEG 8000) administered with:

Treatment A: Standard-Fat with 20-35 wt % fat;
Treatment B: Low-Fat with ~15 wt % fat;
Treatment C: High-Fat with ~50 wt % fat; and
Treatment D: overnight fasting,
to hypogonadal males.

The meals were as follows in Table I with quantity specified as grams (g) or [% total calories].

TABLE I

| Treatment | Total Energy (kcal) | Carbohydrates | Proteins | Lipids |
|---|---|---|---|---|
| A: Standard Fat | 842.5 | 115.2 g [54.7 wt %] | 27.7 g [13.2 wt %] | 30.1 g [32.1 wt %] |
| B: Low Fat | 911.7 | 173 g [75.9 wt %] | 17.8 g [7.8 wt %] | 16.5 g [16.3 wt %] |
| C: High Fat | 930.7 | 82 g [35.2 wt %] | 30.3 g [13.0 wt %] | 53.5 g [51.7 wt %] |

The results from the clinical trial are summarized in Table II below, which demonstrates bioequivalence for Cmax and Cavg for a standard meal versus a low fat meal or high fat meal and low fat versus high fat meals.

TABLE II

| Test Condition | $C_{max}$ (ng/dL) | $C_{avg}$ (ng/dL) |
|---|---|---|
| Point estimate [90% CI bounds] Interpolation of Phase 3 food fat content | | |
| Standard vs. Low | 98 [82-117] | 99 [91-107] |
| Standard Vs. high | 103 [86-123] | 114 [105-124] |

TABLE II-continued

| Test Condition | $C_{max}$ (ng/dL) | $C_{avg}$ (ng/dL) |
|---|---|---|
| Effect of food fat content spread (low to high) | | |
| Low Vs. High | 105 [88-125] | 115 [106-125] |

Thus, it was surprisingly discovered that oral testosterone undecanoate compositions can be administered to hypogonadal males with a meal without fat content of the meal substantially effecting bioavailability. This result is unexpected and in direct contrast to the results obtained with other testosterone undecanoate oral formulations reported in the literature whose bioavailability is dependent on meal fat content.

Given this information one of ordinary skill in the present arts would be capable of providing oral testosterone undecanoate formulation that are bioequivalent to the formulation used in this study, that are bioequivalent for $C_{max}$, $AUC_{(0-t)}$, $AUC_{(0-\infty)}$, $C_{avg}$, or a combination thereof at low, standard, and high fat conditions as well as standard versus low fat, standard versus high fat and low versus high fat.

The results of this study are also summarized in Tables III & IV below.

TABLE III

Comparative Pharmacokinetic Analysis for Testosterone Exposure following Administration of Formulation A under Fed Conditions with Meals of Varying Fat Content (Study, N = 13)

| Parameter | Low Fat (~16.5 g) Meal[2] | Standard Fat (~30.1 g) Meal[1] (Reference) | High Fat (~53.5 g) Meal[3] |
|---|---|---|---|
| Cmax (ng/dL) | | | |
| Mean (% CV) | 1570 (35%) | 1560 (31%) | 1680 (44%) |
| [Range] | [844-2610] | [746-2700] | [692-2910] |
| Point Estimate | 98.26 | 100 | 102.72 |
| (90% CI bounds) | (82.18-117.48) | | (85.92-122.82) |
| AUC 0-24 h (ng * h/dL) | | | |
| Mean (% CV) | 10429 (19%) | 10421 (16%) | 11974 (18%) |
| [Range] | [7529-14083] | [7817-14394] | [8729-15184] |
| Point Estimate | 98.86 | 100 | 114.06 |
| (90% CI bounds) | (90.99-107.42) | | (104.98-123.93) |

Abbreviations:
AUC = area under the curve;
CI = confidence interval;
Cmax = maximum observed serum concentration;
CV = coefficient of variation
[1]30% total calories derived from fat content in the meal consistent with Phase 3 recommended meal
[2]15% total calories derived from fat content in the meal
[3]50% total calories derived from fat content in the meal

TABLE IV

Pharmacokinetic Parameters for Serum Total Testosterone following Formulation A Administration under Fasted vs Fed Conditions in Hypogonadal Men

| Parameter | Fasted (N = 14) | Fed[1] (N = 13) |
|---|---|---|
| Cmax (ng/dL) | | |
| Mean (% CV) | 562 (26%) | 1680 (44%) |
| [Range] | [342-880] | [692-2910] |
| AUC 0-24 h (ng * h/dL) | | |
| Mean (% CV) | 7423 (19%) | 11974 (18%) |
| [Range] | [5597-10787] | [8729-15184] |

Abbreviations:
AUC  area under the curve;
Cmax = maximum observed serum concentration;
CV = coefficient of variation
[1]50% total calories derived from fat content in the meal

TABLE 5

Pharmacokinetics of Dihydrotestosterone

| PK Parameter | Standard Fat | Low Fat | High Fat | Fasted |
|---|---|---|---|---|
| $C_{max}$ (GLSM, ng/dL) | 166 | 152 | 185 | 63 |
| Point estimate [90% CI bounds] | Reference | 92 [81-105] | 111 [98-127] | 38 [34-44] |
| $AUC_{0-t}$ (GLSM, ng * h/dL) | 1580 | 1439 | 1893 | 807 |
| Point estimate [90% CI bounds] | Reference | 91 [82-102] | 120 [107-134] | 51 [46-57] |
| $C_{avg}$ (GLSM, ng/dL) | 66 | 60 | 79 | 34 |
| Point estimate [90% CI bounds] | Reference | 91 [82-102] | 120 [107-134] | 51 [46-57] |

Thus, these results support a drug label indicating that the oral testosterone replacement therapy is taken (1) "WITH A MEAL" or (2) "WITH MEAL, BUT NOT ON EMPTY STOMACH" or (3) "WITH FAT CONTAINING FOOD" not specifying fat content. In the alternative, the drug label may indicate "TAKE IT WITH MEAL, BUT NOT LOW FAT". In another alternative, the drug label may indicate "TAKE IT WITH MEAL, BUT NOT HIGH FAT". It yet another alternative, the drug label may indicate "TAKE IT WITH STANDARD OR NORMAL MEAL".

Example 2

Bioequivalent Formulations and Oral Dosage Forms

The ordinary skilled artisan in view of these results can design and test formulations for bioequivalence (e.g., food effect bioequivalence) using the present disclosure.

Formulations for testing in a food effect study as described in Example 1 (or another appropriate designed study) can be designed e.g., by:

(1) varying the loading of testosterone undecanoate;
(2) varying the amount of Maisine 35-1, exchanging Maisine 35-1 for another lipophilic additive (in varying amounts) or including one or more additional lipophilic additives in addition to Maisine 35-1 (in varying amounts);
(3) varying the amount of Cremophor RH 40, exchanging Cremophor RH 40 for another hydrophilic additive (in varying amounts) or including one or more additional hydrophilic additives in addition to Cremophor RH 40 (in varying amounts);
(4) varying the amount of PEG 8000 (or not include PEG 8000), exchanging PEG 8000 for another solidifying agent (in varying amounts) or including one or more additional solidifying agents in addition to PEG 8000 (in varying amounts);
(5) including one or more additional pharmaceutically acceptable carriers (in varying amounts); or
(6) a combination of one or more of (1)-(5).

Typically, these formulations will be suited for soft gelatin or hard gelatin capsules. Other dosage forms are also contemplated for use in the present disclosure including tablets, sachets, lozenges, granules, powders, sprinkle, suspension, liquids or combinations thereof.

Example 3

Clinical Trial to Show Bioequivalence

To determine if a Test formulation is bioequivalent to the formulation used in Example 1, a bioequivalence study is performed under the same or similar conditions. One of ordinary skill in the art can design and perform a bioequivalence study in view of the results presented in Example 1. Test formulations can be generated according to this disclosure or more particularly Example 2. The bioequivalence study is one that may support the filing of an Abbreviated New Drug Application at the US FDA or similar application in jurisdictions outside of the United States with the appropriate regulatory agency.

It is understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. A method for replacement therapy in a male for a condition associated with a deficiency or absence of endogenous testosterone, said method comprising: orally administering to a male having a condition associated with a deficiency or absence of endogenous testosterone, with a meal having a fat content of a predetermined amount, a pharmaceutical composition comprising from about 50 mg to about 300 mg of testosterone undecanoate and a pharmaceutically acceptable carrier, wherein said administration of said pharmaceutical composition provides bioequivalent amounts of serum testosterone, testosterone undecanoate, dihydrotestosterone, or dihydrotestosterone undecanoate levels to said male regardless of the amount of said fat content of said meal.

2. The method of claim 1, wherein said pharmaceutical composition has about 75 mg, about 112.5 mg, about 150 mg, about 225 mg, or 300 mg of testosterone undecanoate.

3. The method of claim 1, wherein said predetermined amount of fat content of said meal comprises at least one of a high fat content, a standard fat content, and a low fat content.

4. The method of claim 1, wherein said method provides a serum testosterone Cavg in the range of 300 ng/dL to 1100 ng/dL.

5. The method of claim 1, wherein said administering occurs twice-a-day.

6. The method of claim 1, wherein said method comprises administering from 285 mg to about 625 mg of testosterone undecanoate per day.

7. The method of claim 1, wherein said composition comprises a lipophilic additive.

8. The method of claim 1, wherein said composition comprises a hydrophilic additive.

9. The method of claim 1, wherein said pharmaceutical composition (1) is pharmaceutically equivalent to an oral pharmaceutical composition having about 75 mg or about 112.5 mg of testosterone undecanoate at about 15 wt % loading, about 63 wt % glyceryl monolinoleate, about 16 wt % polyoxyl 40 hydrogenated castor oil, and about 6 wt % PEG 8000 or (2) has about 75 mg or about 112.5 mg of testosterone undecanoate at about 15 wt % loading, about 63 wt % glyceryl monolinoleate, about 16 wt % polyoxyl 40 hydrogenated castor oil, and about 6 wt % PEG 8000.

10. The method of claim 1, wherein said method comprises administering the pharmaceutical composition as 2, 3, 4, 5, 6, 7, or 8 unit dosage forms per day.

11. A method for replacement therapy in a male for conditions associated with a deficiency or absence of endogenous testosterone, said method comprising: orally administering to a male having a condition associated with a deficiency or absence of endogenous testosterone, with a meal having about 10 wt % to 50 wt % fat, a pharmaceutical composition comprising from about 50 mg to about 300 mg of testosterone undecanoate and a pharmaceutically acceptable carrier, wherein said pharmaceutical composition provides bioequivalent amounts of serum testosterone, testosterone undecanoate, dihydrotestosterone, or dihydrotestosterone undecanoate levels to said male regardless of the wt % fat of said meal.

12. The method of claim 11, wherein said pharmaceutical composition (1) is pharmaceutically equivalent to an oral pharmaceutical composition having about 75 mg or about 112.5 mg of testosterone undecanoate at about 15 wt % loading, about 63 wt % glyceryl monolinoleate, about 16 wt % polyoxyl 40 hydrogenated castor oil, and about 6 wt % PEG 8000 or (2) has about 75 mg or about 112.5 mg of testosterone undecanoate at about 15 wt % loading, about 63 wt % glyceryl monolinoleate, about 16 wt % polyoxyl 40 hydrogenated castor oil, and about 6 wt % PEG 8000.

13. The method of claim 11, wherein said method provides a serum testosterone Cavg in the range of 300 ng/dl to 1100 ng/dL.

14. The method of claim 11, wherein said method comprises administering from 285 mg to about 625 mg of testosterone undecanoate per day.

15. The method of claim 11, said administering occurs twice-a-day.

16. The method of claim 1, wherein said pharmaceutical composition has about 75 mg, about 112.5 mg, about 150 mg, about 225 mg, or 300 mg of testosterone undecanoate, and wherein said pharmaceutically acceptable carrier is selected to provide bioequivalent amounts of serum testosterone levels to said male for meals containing low fat, standard fat and high fat, and wherein said method provides a serum testosterone Cavg in the range of 300 ng/dl to 1100 ng/dL, and wherein said administering occurs twice-a-day, and wherein said method comprises administering from 285 mg to about 625 mg of testosterone undecanoate per day.

17. The method of claim 16, wherein said composition comprises a lipophilic additive and a hydrophilic additive.

18. The method of claim 16, wherein said pharmaceutical composition (1) is pharmaceutically equivalent to an oral pharmaceutical composition having about 75 mg or about 112.5 mg of testosterone undecanoate at about 15 wt % loading, about 63 wt % glyceryl monolinoleate, about 16 wt % polyoxyl 40 hydrogenated castor oil, and about 6 wt % PEG 8000 or (2) has about 75 mg or about 112.5 mg of testosterone undecanoate at about 15 wt % loading, about 63 wt % glyceryl monolinoleate, about 16 wt % polyoxyl 40 hydrogenated castor oil, and about 6 wt % PEG 8000.

19. The method of claim 16, wherein said method comprises administering the pharmaceutical composition as 2, 3, 4, 5, 6, 7, or 8 unit dosage forms per day.

20. A method for replacement therapy in a male for a condition associated with a deficiency or absence of endogenous testosterone, said method comprising: orally administering to a male having a condition associated with a deficiency or absence of endogenous testosterone, with a meal, a pharmaceutical composition comprising testosterone undecanoate and a pharmaceutically acceptable carrier, wherein said pharmaceutical composition provides bioequivalent amounts of serum testosterone, testosterone undecanoate, dihydrotestosterone, or dihydrotestosterone undecanoate levels to said male when administered with meals containing at least one of standard fat, low fat, and high fat, wherein said method provides a serum testosterone Cavg in the range of 300 ng/dl to 1100 ng/dL, and wherein said administering occurs twice-a-day, and wherein said method comprises administering from 285 mg to about 625 mg of testosterone undecanoate per day, and wherein said composition comprises a lipophilic additive and a hydrophilic additive, and wherein said method comprises administering the pharmaceutical composition as 2, 3, 4, 5, 6, 7, or 8 unit dosage forms per day.

\* \* \* \* \*